United States Patent

Zagar et al.

[11] Patent Number: 6,054,413
[45] Date of Patent: Apr. 25, 2000

[54] 1-SULFONYL-3-PHENYLPYRAZOLES AND THEIR USE AS HERBICIDES AND FOR DESICCATING OR DEFOLIATING PLANTS

[75] Inventors: Cyrill Zagar, Ludwigshafen; Gerhard Hamprecht, Weinheim; Markus Menges, Mannheim; Olaf Menke, Altleiningen; Peter Schäfer, Ottersheim; Karl-Otto Westphalen, Speyer; Ulf Misslitz, Neustadt; Helmut Walter, Obrigheim, all of Germany

[73] Assignee: BASF Aktiengesellschaft, Ludwigshafen, Germany

[21] Appl. No.: 09/254,923

[22] PCT Filed: Sep. 9, 1997

[86] PCT No.: PCT/EP97/04911

§ 371 Date: Mar. 17, 1999

§ 102(e) Date: Mar. 17, 1999

[87] PCT Pub. No.: WO98/12182

PCT Pub. Date: Mar. 26, 1998

[30] Foreign Application Priority Data

Sep. 19, 1996 [DE] Germany ............... 196 38 234

[51] Int. Cl.$^7$ ............... A01N 43/56; A01N 43/84; C07D 231/14; C07D 413/12
[52] U.S. Cl. ............... 504/169; 504/280; 544/140; 546/211; 548/119; 548/364.1; 548/365.7; 548/376.1
[58] Field of Search ............... 548/376.1; 504/169, 504/280

[56] References Cited

U.S. PATENT DOCUMENTS 4,969,948  11/1990  Haug et al. .
5,281,571  1/1994  Woodard et al. .
5,510,320  4/1996  Tseng .
5,523,280  6/1996  Chene et al. .................. 548/376.1

FOREIGN PATENT DOCUMENTS 009998   4/1980  European Pat. Off. .
230110   7/1987  European Pat. Off. .
92/02509 2/1992  WIPO .
96/02515 2/1996  WIPO .
97/15559 5/1997  WIPO .

OTHER PUBLICATIONS

Bull. de la Soc. Chim de France 2 Partie–Chimie Org., Biochimie., No. 3–4, 1982, pp. 89–94.
J. of Heterocyclic Chem., vol. 23, No. 2, 1986, pp. 459–461.

Primary Examiner—Robert W. Ramsuer
Attorney, Agent, or Firm—Keil & Weinkauf

[57] ABSTRACT

The present invention relates to novel 1-sulfonyl-3-phenylpyrazoles of the formula I

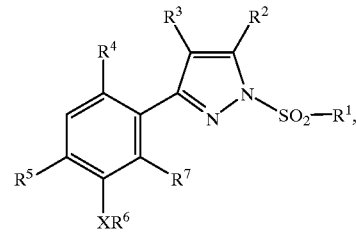

and agriculturally useful salts of I.

Furthermore, the invention relates to
  the use of the compounds I as herbicides and/or for the desiccation and/or defoliation of plants,
  herbicidal compositions and compositions for the desiccation and/or defoliation of plants which comprise the compounds I as active ingredients,

10 Claims, No Drawings

1-SULFONYL-3-PHENYLPYRAZOLES AND THEIR USE AS HERBICIDES AND FOR DESICCATING OR DEFOLIATING PLANTS

1-Sulfonyl-3-phenylpyrazoles

The present invention relates to novel 1-sulfonyl-3-phenylpyrazoles of the formula I

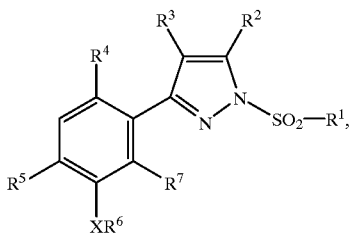

where:
$R^1$ is $C_1$–$C_4$-alkyl or $C_1$–$C_4$-haloalkyl;
$R^2$ is $C_1$–$C_4$-alkyl or $C_1$–$C_4$-haloalkyl;
$R^3$ is hydrogen, cyano, halogen or $C_1$–$C_4$-alkyl;
$R^4$ is hydrogen or halogen;
$R^5$ is hydrogen, cyano, nitro, halogen, $C_1$–$C_4$-alkyl, $C_1$–$C_4$-haloalkyl, $C_1$–$C_4$-alkoxy or $C_1$–$C_4$-haloalkoxy;
X is a chemical bond or a methylene, ethylene, propane-1,3-diyl or ethene-1,2-diyl chain or an oxymethylene or thiamethylene chain linked to the phenyl ring via the hetero atom, all chains being unsubstituted or substituted by one or two substituents selected in each case from the group consisting of cyano, carboxyl, halogen, $C_1$–$C_4$-alkyl, $C_1$–$C_4$-haloalkyl, $C_1$–$C_4$-alkoxy, ($C_1$–$C_4$-alkoxy)carbonyl, di($C_1$–$C_4$-alkyl)amino and phenyl;
$R^6$ is hydrogen, nitro, cyano, halogen, halosulfonyl, —O—Y—$R^8$, —O—CO—Y—$R^8$, —N(Y—$R^8$)(Z—$R^9$), —N(Y—$R^8$)—$SO_2$—Z—$R^9$, —N($SO_2$—Y—$R^8$)($SO_2$—Z—$R^9$), —N(Y—$R^8$)—CO—Z—$R^9$, —N(Y—$R^8$)(O—Z—$R^9$), —S—Y—$R^8$, —SO—Z—$R^8$, —$SO_2$—Y—$R^8$, —$SO_2$—O—Y—$R^8$, —$SO_2$—N(Y—$R^8$)(Z—$R^9$), —CO—Y—$R^8$, —C(=N$OR^{10}$)—Y—$R^8$, —C(=N$OR^{10}$)—O—Y—$R^8$, —CO—O—Y—$R^8$, —CO—S—Y—$R^8$, —CO—N(Y—$R^8$)(Z—$R^9$) —CO—N(Y—$R^8$)(O—Z—$R^9$) or —PO(O—Y—$R^8$)$_2$;
$R^7$ is hydrogen,
or $R^5$ and $XR^6$ or $XR^6$ and $R^7$ form together with the carbons of the phenyl ring linking them a fused carbocyclic or 5- or 6-membered heterocyclic ring having 1 to 3 hetero atoms selected from a group consisting of one to three nitrogens, one or two oxygens and one or two sulfur atoms, the fused ring being unsubstituted or substituted by one or two substituents selected in each case from the group consisting of $C_1$–$C_4$-alkyl, $C_1$–$C_4$-haloalkyl, $C_2$–$C_6$-alkenyl, $C_2$–$C_6$-haloalkenyl, $C_2$–$C_6$-alkynyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl, $C_1$–$C_4$-haloalkylsulfonyl, ($C_1$–$C_4$-alkoxy)carbonyl, ($C_1$–$C_4$-alkoxy)carbonyl-$C_1$–$C_4$-alkyl, phenyl and phenyl-$C_1$–$C_4$-alkyl, it being possible for the fused cycle to contain one or two non-neighboring carbonyl, thiocarbonyl or sulfonyl ring members;
Y and Z are each independently of each other a chemical bond or a methylene or ethylene chain which may be unsubstituted or substituted by one or two substituents selected in each case from the group consisting of carboxyl, $C_1$–$C_4$-alkyl, $C_1$–$C_4$-haloalkyl, ($C_1$–$C_4$-alkoxy)carbonyl and phenyl;

$R^8$ and $R^9$ are each independently of each other hydrogen, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, —CH($R^{11}$)($R^{12}$), —C($R^{11}$)($R^{12}$)—$NO_2$, —C($R^{11}$)($R^{12}$)—CN, —C($R^{11}$)($R^{12}$)-halogen, —C($R^{11}$)($R^{12}$)—$OR^{13}$, —C($R^{11}$)($R^{12}$)—N($R^{13}$)$R^{14}$, —C($R^{11}$)($R^{12}$)—N($R^{13}$)—$OR^{14}$, —C($R^{11}$)($R^{12}$)—$SR^{13}$, —C($R^{11}$)($R^{12}$)—SO—$R^{13}$, —C($R^{11}$)($R^{12}$)—$SO_2$—$R^{13}$, —C($R^{11}$)($R^{12}$)—$SO_2$C—$OR^{13}$, —C($R^{11}$)($R^{12}$)—$SO_2$—N($R^{13}$)$R^{14}$, —C($R^{11}$)($R^{12}$)—$COR^{13}$, —C($R^{11}$)($R^{12}$)—C(=N$OR^{15}$)—$R^{13}$, —C($R^{11}$)($R^{12}$)—CO—$SR^{13}$, —C($R^{11}$)($R^{12}$)—CO—N($R^{13}$)$R^{14}$, —C($R^{11}$)($R^{12}$)—CO—N($R^{13}$)—$OR^{14}$, —C($R^{11}$)($R^{12}$)—PO($OR^{13}$)$_2$, $C_3$–$C_8$-cycloalkyl which may contain a carbonyl or thiocarbonyl ring member, phenyl or 3- to 7-membered heterocyclyl which may contain a carbonyl or thiocarbonyl ring member, the cycloalkyl, phenyl and heterocyclyl rings being in each case unsubstituted or substituted by one to four substituents selected in each case from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy, ($C_1$–$C_4$-alkoxy)carbonyl and di-($C_1$–$C_4$-alkyl)amino;
$R^{10}$ is hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalkyl, phenyl or phenyl-$C_1$–$C_4$-alkyl;
$R_{11}$ and $R^{12}$ are each independently of each other hydrogen, $C_1$–$C_4$-alkyl, $C_1$–$C_4$-alkoxy-$C_1$–$C_4$-alkyl, $C_1$–$C_4$-alkylthio-$C_1$–$C_4$-alkyl, ($C_1$–$C_4$-alkoxy)carbonyl-$C_1$–$C_4$-alkyl or phenyl-$C_1$–$C_4$-alkyl, the phenyl ring being unsubstituted or substituted by one to three substituents selected in each case from the group consisting of cyano, nitro, carboxyl, halogen, $C_1$–$C_4$-alkyl, $C_1$–$C_4$-haloalkyl and ($C_1$–$C_4$-alkoxy)carbonyl;
$R^{13}$ and $R^{14}$ are each independently of each other hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalkyl, $C_3$–$C_8$-cycloalkyl-$C_1$–$C_4$-alkyl, phenyl, phenyl-$C_1$–$C_4$-alkyl, 3- to 7-membered heterocyclyl or heterocyclyl-$C_1$–$C_4$-alkyl, where each cycloalkyl and each heterocyclyl ring may contain a carbonyl or thiocarbonyl ring member and where the cycloalkyl, phenyl and heterocyclyl rings may in each case be unsubstituted or substituted by one to four substituents selected in each case from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy, ($C_1$–$C_4$-alkoxy)carbonyl and di($C_1$–$C_4$-alkyl)amino;
$R^{15}$ is hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalkyl, phenyl or phenyl-$C_1$–$C_4$-alkyl;
and agriculturally useful salts of I.

Furthermore, the invention relates to
the use of the compounds I as herbicides and/or for the desiccation and/or defoliation of plants,
herbicidal compositions and compositions for the desiccation and/or defoliation of plants which comprise the compounds I as active ingredients, processes for preparing the compounds I and herbicidal compositions and compositions for the desiccation and/or defoliation of plants using the compounds I, and methods for controlling undesirable vegetation and for the desiccation and/or defoliation of plants using the compounds I.

Those compounds I where $R^1$ and $R^2$ are both $C_1$–$C_4$-alkyl, $R^4$, $R^5$, $R^6$ and $R^7$ are all hydrogen and X is a chemical bond are formally covered by the general formula of the peroxide activators disclosed in EP-A 009 998.

U.S. Pat. No. 5,510,320 discloses herbicidal triazolylsulfonylpyrazoles. WO 92/02509 discloses herbicidal phenyl(alkylsulfonyl)pyrazoles.

The herbicidal properties of the prior art pyrazoles with regard to the harmful plants are not always entirely satisfactory.

It is an object of the present invention to provide novel 3-phenylpyrazoles which allow better selective control of undesirable plants. It is a further object to provide novel compounds which have a desiccant/defoliant action.

We have found that these objects are achieved by the present 1-sulfonyl-3-phenylpyrazoles of the formula I.

Furthermore, we have found herbicidal compositions which comprise the compounds I and have a very good herbicidal activity. Moreover, we have found processes for preparing these compositions and methods for controlling undesirable vegetation using the compounds I.

Furthermore, we have found that the compounds I are also suitable for the desiccation/defoliation of parts of plants, suitable plants being crop plants such as cotton, potatoes, oil seed rape, sunflower, soybean or field beans, in particular cotton. Thus, we have found compositions for the desiccation and/or defoliation of plants, processes for preparing these compositions and methods for the desiccation and/or defoliation of plants using the compounds I.

Depending on the substitution pattern, the compounds of the formula I can contain one or more chiral centers, in which case they exist in the form of enantiomer or diastereomer mixtures. The invention relates to the pure enantiomers or diastereomers and also to mixtures thereof.

The organic moieties mentioned in the definition of the substituents $R^1$, $R^2$, $R^5$ and $R^8$ to $R^{15}$ or as radicals on cycloalkyl, phenyl or heterocyclyl rings or on X, Y and Z are—like the term halogen—collective terms for individual listings of the individual group members. All carbon chains, i.e. all alkyl, haloalkyl, phenylalkyl, cycloalkylalkyl, alkoxy, haloalkoxy, alkylthio, haloalkylthio, alkylsulfinyl, haloalkylsulfinyl, alkylsulfonyl, haloalkylsulfonyl, alkenyl, haloalkenyl, alkynyl and haloalkynyl moieties, can be straight-chain or branched. Halogenated substituents preferably have attached to them one to five identical or different halogens. The term halogen represents in each case fluorine, chlorine, bromine or iodine.

Other examples of meanings are, for example:

$C_1$–$C_4$-alkyl: $CH_3$, $C_2H_5$, n-propyl, $CH(CH_3)_2$, n-butyl, $CH(CH_3)$–$C_2H_5$, $CH_2$–$CH(CH_3)_2$ and $C(CH_3)_3$;

$C_1$–$C_4$-haloalkyl: a $C_1$–$C_4$-alkyl radical as mentioned above which is partially or fully substituted by fluorine, chlorine, bromine and/or iodine, i.e. for example $CH_2F$, $CHF_2$, $CF_3$, $CH_2Cl$, dichloromethyl, trichloromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-fluoromethyl-2-fluoroetbyl, 1-chloromethyl-2-chloroethyl, 1-bromomethyl-2-bromoethyl, 4-fluorobutyl, 4-chlorobutyl, 4-bromobutyl and nonafluorobutyl;

$C_1$–$C_6$-alkyl: $C_1$–$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$–$C_6$-haloalkyl: a $C_1$–$C_6$-alkyl radical as mentioned above which is partially or fully substituted by fluorine, chlorine, bromine and/or iodine, i.e. for example one of the radicals mentioned under $C_1$–$C_4$-haloalkyl, and also 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl;

phenyl-$C_1$–$C_4$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-phenylmethyleth-1-yl, 1-phenylmethyl-1-methyleth-1-yl or 1-phenylmethylprop-1-yl, preferably benzyl or 2-phenylethyl;

$C_3$–$C_8$-cycloalkyl-$C_1$–$C_4$-alkyl: cyclopropylmethyl, 1-cyclo-propylethyl, 2-cyclopropylethyl, 1-cyclopropylprop-1-yl, 2-cyclopropylprop-1-yl, 3-cyclopropylprop-1-yl, 1-cyclo-propylbut-1-yl, 2-cyclopropylbut-1-yl, 3-cyclopropylbut-1-yl, 4-cyclopropylbut-1-yl, 1-cyclopropylbut-2-yl, 2-cyclopropyl-but-2-yl, 3-cyclopropylbut-2-yl, 3-cyclopropylbut-2-yl, 4-cyclopropylbut-2-yl, 1-cyclopropylmethyleth-1-yl, 1-cyclo-propylmethyl-1-methyleth-1-yl, 1-cyclopropylmethylprop-1-yl, cyclobutylmethyl, 1-cyclobutylethyl, 2-cyclobutylethyl, 1-cyclobutylprop-1-yl, 2-cyclobutylprop-1-yl, 3-cyclobutyl-prop-1-yl, 1-cyclobutylbut-1-yl, 2-cyclobutylbut-1-yl, 3-cyclobutylbut-1-yl, 4-cyclobutylbut-1-yl, 1-cyclobutyl-but-2-yl, 2-cyclobutylbut-2-yl, 3-cyclobutylbut-2-yl, 3-cyclobutylbut-2-yl, 4-cyclobutylbut-2-yl, 1-cyclobutyl-methyleth-1-yl, 1-cyclobutylmethyl-1-methyleth-1-yl, 1-cyclobutylmethylprop-1-yl, cyclopentylmethyl, 1-cyclo-pentylethyl, 2-cyclopentylethyl, 1-cyclopentylprop-1-yl, 2-cyclopentylprop-1-yl, 3-cyclopentylprop-1-yl, 1-cyclo-pentylbut-1-yl, 2-cyclopentylbut-1-yl, 3-cyclopentylbut-1-yl1 4-cyclopentylbut-1-yl, 1-cyclopentylbut-2-yl, 2-cyclopentyl-but-2-yl, 3-cyclopentylbut-2-yl, 3-cyclopentylbut-2-yl, 4-cyclopentylbut-2-yl, 1-cyclopentylmethyleth-1-yl, 1-cyclo-pentylmethyl-1-methyleth-1-yl, 1-cyclopentylmethylprop-1-yl, cyclohexylmethyl, 1-cyclohexylethyl, 2-cyclohexylethyl, 1-cyclohexylprop-1-yl, 2-cyclohexylprop-1-yl, 3-cyclohexyl-prop-1-yl, 1-cyclohexylbut-1-yl, 2-cyclohexylbut-1-yl, 3-cyclohexylbut-1-yl, 4-cyclohexylbut-1-yl, 1-cyclohexyl-but-2-yl, 2-cyclohexylbut-2-yl, 3-cyclohexylbut-2-yl, 3-cyclohexylbut-2-yl, 4-cyclohexylbut-2-yl, 1-cyclohexyl-methyleth-1-yl, 1-cyclohexylmethyl-1-methyleth-1-yl, 1-cyclohexylmethylprop-1-yl, cycloheptylmethyl, 1-cyclo-heptylethyl, 2-cycloheptylethyl, 1-cycloheptylprop-1-yl, 2-cycloheptylprop-1-yl, 3-cycloheptylprop-1-yl, 1-cyclo-heptylbut-1-yl, 2-cycloheptylbut-1-yl, 3-cycloheptylbut-1-yl, 4-cycloheptylbut-1-yl, 1-cycloheptylbut-2-yl, 2-cycloheptyl-but-2-yl, 3-cycloheptylbut-2-yl, 3-cycloheptylbut-2-yl, 4-cycloheptylbut-2-yl, 1-cycloheptylmethyleth-1-yl, 1-cyclo-heptylmethyl-1-methyleth- 1-yl, 1-cycloheptylmethylprop-1-yl, cyclooctylmethyl, 1-cyclooctylethyl, 2-cyclooctylethyl, 1-cyclooctylprop-1-yl, 2-cyclooctylprop-1-yl, 3-cyclooctyl-prop-1-yl, 1-cyclooctylbut-1-yl, 2-cyclooctylbut-1-yl, 3-cyclooctylbut-1-yl, 4-cyclooctylbut-1-yl, 1-cyclooctyl-but-2-yl, 2-cyclooctylbut-2-yl, 3-cyclooctylbut-2-yl-3-cyclooctylbut-2-yl, 4-cyclooctylbut-2-yl, 1-cyclooctyl-methyleth-1-yl, 1-cyclooctylmethyl-1-methyleth-1-yl or 1-cyclooctylmethylprop-1-yl;

$C_3$–$C_8$-cycloalkyl-$C_1$–$C_4$-alkyl containing a carbonyl or thiocarbonyl ring member: for example cyclobutanon-2-yl-methyl, cyclobutanon-3-ylmethyl, cyclopentanon-2-ylmethylr cyclopentanon-3-ylmethyl, cyclohexanon-2-ylmethyl, cyclo-hexanon-4-ylmethyl, cycloheptanon-2-ylmethyl, cyclooctanon-2-ylmethyl, cyclobutanethion-2-ylmethyl, cyclobutanethion-3-ylmethyl, cyclopentanethion-2-ylmethyl, cyclopentanethion-3-ylmethyl, cyclohexanethion-2-ylmethyl, cyclohexanethion-4-ylmethyl, cycloheptanethion-2-ylmethyl, cyclooctanethion-2-ylmethyl, 1-cyclobutanon-2-ylethyl, 1-cyclobutanon-3-yl-2-ylmethyl, 1-cyclopentanon-2-ylethyl, 1-cyclopentanon-3-ylethyl, 1-cyclohexanon-2-ylethyl, 1-cyclohexanon-4-ylethyl, 1-cyclo-heptanon-2-ylethyl, 1-cyclooctanon-2-ylethyl, 1-cyclobutane-thion-2-ylethyl, 1-cyclobutanethion-3-ylethyl, 1-cyclopentanethion-2-ylethyl, 1-cyclopentanethion-3-ylethyl, 1-cyclohexanethion-2-ylethyl, 1-cyclohexanethion-4-ylethyl, 1-cycloheptanethion-2-ylethyl, 1-cyclooctanethion-2-ylethyl, 2-cyclobutanon-2-ylethyl, 2-cyclobutanon-3-ylethyl, 2-cyclopentanon-2-ylethyl, 2-cyclopentanon-3-ylethyl, 2-cyclohexanon-2-ylethyl, 2-cyclohexanon-4-ylethyl, 2-cycloheptanon-2-ylethyl, 2-cyclooctanon-2-ylethyl, 2-cyclobutanethion-2-ylethyl, 2-cyclobutanethion-3-ylethyl, 2-cyclopentanethion-2-ylethyl, 2-cyclopentanethion-3-ylethyl, 2-cyclohexanethion-2-ylethyl, 2-cyclohexanethion-4-ylethyl, 2-cycloheptanethion-2-ylethyl, 2-cyclooctanethion-2-ylethyl, 3-cyclobutanon-2-yl-propyl, 3-cyclobutanon-3-ylpropyl, 3-cyclopentanon-2-yl-propyl, 3-cyclopentanon-3-ylpropyl, 3-cyclohexanon-2-yl-propyl, 3-cyclohexanon-4-ylpropyl, 3-cycloheptanon-2-yl-propyl, 3-cyclooctanon-2-ylpropyl, 3-cyclobutanethion-2-yl-propyl, 3-cyclobutanethion-3-ylpropyl, 3-cyclopentanethion-2-ylpropyl, 3-cyclopentanethion-3-ylpropyl, 3-cyclohexane-thion-2-ylpropyl, 3-cyclohexanethion-4-ylpropyl, 3-cyclo-heptanethion-2-ylpropyl, 3-cyclooctanethion-2-ylpropyl, 4-cyclobutanon-2-ylbutyl, 4-cyclobutanon-3-ylbutyl, 4-cyclo-pentanon-2-ylbutyl, 4-cyclopentanon-3-ylbutyl, 4-cyclo-hexanon-2-ylbutyl, 4-cyclohexanon-4-ylbutyl, 4-cycloheptanon-2-ylbutyl, 4-cyclooctanon-2-ylbutyl, 4-cyclobutanethion-2-ylbutyl, 4-cyclobutanethion-3-ylbutyl, 4-cyclopentanethion-2-ylbutyl, 4-cyclopentanethion-3-ylbutyl, 4-cyclohexane-thion-2-ylbutyl, 4-cyclohexanethion-4-ylbutyl, 4-cyclo-heptanethion-2-ylbutyl or 4-cyclooctanethion-2-ylbutyl;

heterocyclyl-$C_1$–$C_4$-alkyl: heterocyclylmethyl, 1-heterocyclyl-ethyl, 2-heterocyclylethyl, 1-heterocyclylprop-1-yl, 2-heterocyclylprop-1-yl, 3-heterocyclylprop-1-yl, 1-hetero-cyclylbut-1-yl, 2-heterocyclylbut-1-yl 3-heterocyclyl-but-1-yl, 4-heterocyclylbut-1-yl, 1-heterocyclylbut-2-yl, 2-heterocyclylbut-2-yl, 3-heterocyclylbut-2-yl, 3-hetero-cyclylbut-2-yl, 4-heterocyclylbut-2-yl, 1-heterocyclylmethyl-eth-1-yl, 1-heterocyclylmethyl-1-methyleth-1-yl or 1-heterocyclylmethylprop-1-yl, preferably heterocyclylmethyl or 2-heterocyclylethyl;

$C_1$–$C_4$-alkoxy: $OCH_3$, $OC_2B_5$, n-propoxy, $OCH(CH_3)_2$, n-butoxy, $OCH(CH_3)$–$C_2H_5$, $OCH_2$—$CH(CH_3)_2$ or $OC(CH_3)_3$, preferably $OCH_3$, $OC_2H_5$, or $OCH(CH_3)_2$;

$C_1$–$C_4$-haloalkoxy: a $C_1$–$C_4$-alkoxy radical as mentioned above which is partially or fully substituted by fluorine, chlorine, bromine and/or iodine, i.e. for example $OCH_2F$, $OCHF_2$, $OCF_3$, $OCH_2C_1$, $OCH(C_1)_2$, $OC(Cl)_3$, chlorofluoromethoxy, dichlorofluoromethoxy, chlorodifluoromethoxy, 2-fluoroethoxy, 2-chloroethoxy, 2-bromo-ethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, $OCF_2$–$C_2F_5$, 1,-$(CH_2F)$-2-fluoroethoxy, 1-$(CH_2Cl)$-2-chloroethoxy, 1-$(CH_2Br)$-2-bromoethoxy, 4-fluorobutoxy, 4-chlorobutoxy, 4-bromobutoxy or nonafluorobutoxy, preferably $OCHF_2$, $OCF_3$, dichlorofluoromethoxy, chlorodifluoromethoxy or 2,2,2-trifluoroethoxy;

$C_1$–$C_6$-alkylthio: $SCH_3$, $SC_2H_5$, n-propylthio, $SCH(CH_3)_2$, n-butylthio, $SCH(CH_3)$–$C_2C_5$, $SCH2$—$C(CH_3)_2$ or $SC(CH_3)_3$, preferably $SCH_3$ or $SC_2H_5$;

$C_1$–$C_4$-haloalkylthio: a $C_1$–$C_4$-alkylthio radical as mentioned above which is partially or fully substituted by fluorine, chlorine, bromine and/or iodine, i.e. for example $SCH_2F$, $SCHF_2$, $SCH_2C_1$, $SCH(Cl)_2$, $SC(C_1)_3$, $SCF_3$, chlorofluoromethylthio, dichlorofluoromethylthio, chlorodifluoromethylthio, 2-fluoroethylthio, 2-chloroethylthio, 2-bromoethylthio, 2-iodoethylthio, 2 r2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$, 2-fluoropropylthio, 3-fluoropropylthio, 2,2-difluoro-propylthio, 2,3-difluoropropylthio, 2-chloropropylthio, 3-chloropropylthio, 2,3-dichloropropylthio, 2-bromopropyl-thio, 3-bromopropylthio, 3,3,3-trifluoropropylthio, 3,3,3-trichloropropylthio, $SCH_2$–$C_2F_5$, $SCF_2$–$C_2F_5$, 1-$(CH_2F)$-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or $SCF_2$-$CF_2$-$C_2F_5$, preferably $SCBF_2$, $SCF_3$, dichlorofluoromethyl-thio, chlorodifluoromethylthio or 2,2,2-trifluoroethylthio;

$C_1$-$C_4$-alkoxy-$C_1$-$C_4$-alkyl: $C_1$-$C_4$-alkyl which is substituted by $C_1$-$C_4$-alkoxy as mentioned above, i.e. for example $CH_2$-$OCH_3$, $CH_2$-$OC_2H_5$, n-propoxymethyl, $CH_2$-$OCH(CH_3)_2$ n-butoxymethyl, (1-methylpropoxy)methyl, (2-metbylpropoxy)methyl, $CH_2$-$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methyl-propoxy)ethyl, 2-(1,1-dimethylethoxy)ethyl, 2-(methoxy)-propyl, 2-(ethoxy)propyl, 2-(n-propoxy)propyl, 2-(1-methyl-ethoxy) propyl, 2-(n-butoxy)propyl, 2-(l-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methyl-propoxy) propyl, 3-(2-methylpropoxy)propyl, 3-(1,1-dimethyl-ethoxy) propyl, 2-(methoxy)butyl, 2-(ethoxy) butyl, 2-(n-propoxy)butyl, 2-(1-methylethoxy)butyl, 2-(n-butoxy)-butyl, 2-(1-methylpropoxy)butyl, 2-(2-methylpropoxy)butyl, 2-(1,1-dimethylethoxy)butyl, 3-(methoxy)butyl, 3-(ethoxy)-butyl, 3-(n-propoxy)butyl, 3-(1-methylethoxy)butyl, 3-(n-butoxy)butyl, 3-(1-methylpropoxy)butyl, 3-(2-methyl-propoxy)butyl, 3-(1,1-dimethylethoxy)butyl, 4-(methoxy)butyl, 4-(ethoxy)butyl, 4-(n-propoxy)butyl, 4-(I-methylethoxy)butyl, 4-(n-butoxy)butyl, 4-(methylpropoxy)butyl, 4-(2-methyl-propoxy) butyl or 4-(1,1-dimethylethoxy)butyl, preferably $CH_2$—$OCH_3$, $CH_2$—$OC_2H_5$, 2-methoxyethyl or 2-ethoxyethyl;

$C_1$-$C_4$-alkylthio-$C_1$-$C_4$-alkyl: $C_1$-$C_4$-alkyl which is substituted by $C_1$-$C_4$-alkylthio as mentioned above, i.e. for example $CH_2$-$SCH_3$, $CH_2$-$SC_2H_5$, n-propylthiomethyl, $CH_2$—$SCH(CH_3)_2$ n-butylthiomethyl, (1-methylpropylthio)methyl, (2-methylpropylthio)methyl, $CH_2$-$SC(CH_3)_{31}$ 2-(methylthio)ethyl, 2-(ethylthio)ethyl, 2-(n-propylthio)ethyl, 2-(-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 2-(ethylthio)propyl, 2-(n-propylthio)-propyl, 2-(1-methylethylthio)propyl, 2-(n-butylthio)propyl, 2-(1-methylpropylthio)propyl, 2-(2-methylpropylthio)propyl, 2-(1,1-dimethylethylthio)propyl, 3-(methylthio)propyl, 3-(ethylthio)propyl, 3-(n-propylthio)propyl, 3-(1-methyl-ethylthio) propyl, 3-(n-butylthio)propyl, 3-(1-methylpropyl-thio) propyl, 3-(2-methylpropylthio)propyl, 3-(1,1-dimethyl-ethylthio)propyl, 2-(methylthio)butyl, 2-(ethylthio)butyl, 2-(n-propylthio)butyl, 2-(1-methylethylthio)butyl, 2-(n-butylthio)butyl, 2-(1-methylpropylthio) butyl, 2-(2-methylpropylthio)butyl, 2-(1,1-dimethylethylthio)butyl, 3-(methylthio)butyl, 3-(ethylthio)butyl, 3-(n-propylthio)-butyl, 3-(1-methylethylthio)butyl, 3-(n-butylthio)butyl, 3-(1-methylpropylthio)butyl, 3-(2-methylpropylthio)butyl, 3-(1,1-dimethylethylthio)butyl, 4-(methylthio)butyl, 4-(ethylthio)butyl, 4-(n-propylthio)butyl, 4-(1-methyl-ethylthio)butyl, 4-(n-butylthio)butyl, 4-(1-methylpropyl-thio)butyl, 4-(2-methylpropylthio)butyl or 4-(1,1-dimethyl-ethylthio)butyl, preferably $CH_2$-$SCH_3$, $CH_2$-$SC_2H_5$, 2-methylthioethyl or 2-ethylthioethyl;

($C_1$-$C_4$-alkyl)carbonyl: CO—$CH_3$, CO—$C_2H_5$, CO—$CR_2$—$C_2H_5$, CO—$CH(CH_3)_2$, n-butylcarbonyl, CO—$CH(CH_3)$-$C_2H_5$, CO—$CH_2$—$CH(CH_3)_2$ or $C_0$—$C(CH_3)_3$, preferably CO—$CH_3$ or CO—$C_2H_5$;

($C_1$-$C_4$-haloalkyl)carbonyl: a ($C_1$-$C_4$-alkyl)carbonyl radical as mentioned above which is partially or fully substituted by fluorine, chlorine, bromine and/or iodine, i.e. for example CO—$CH_2F$, CO—$CHF_2$, CO—$CF_3$, CO—$CH_2C_1$, CO—$CH(C_1)_2$, $C_0$—$nC(C_1)_3$, chlorofluoromethylcarbonyl, dichlorofluoromethylcarbonyl, chlorodifluoromethylcarbonyl, 2-fluoroethylcarbonyl, 2-chloroethylcarbonyl, 2-bromoethylcarbonyl, 2-iodoethyl-carbonyl, 2,2-difluoroethylcarbonyl, 2,2,2-trifluoroethyl-carbonyl, 2-chloro-2-fluoroethylcarbonyl, 2-chloro-2,2-difluoroethylcarbonyl, 2,2-dichloro-2-fluoroethyl-carbonyl, 2,2,2-trichloroethylcarbonyl, CO—$C_2F_5$, 2-fluoro-propylcarbonyl, 3-fluoropropylcarbonyl, 2,2-difluoropropyl-carbonyl, 2,3-difluoropropylcarbonyl, 2-chloropropyl-carbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, CO—$CF_2$-$C_2F_5$, 1($CH_2F$)-2-fluoroethylcarbonyl, 1-($CH_2C_1$)-2-chloro-ethylcarbonyl, 1-($CH_2Br$)-2-bromoethylcarbonyl, 4-fluorobutyl-carbonyl, 4-chlorobutylcarbonyl, 4-bromobutylcarbonyl or nonafluorobutylcarbonyl, preferably CO—$CF_3$, CO—$CH_2C_1$ or 2,2,2-trifluoroethylcarbonyl;

($C_1$-$C_4$-alkyl)carbonyloxy: O—CO—$H_3$, O—CO—$C_2HS$, O—CO—$CH_2$-$C_2H_5$, O—CO—$CH(CH_3)_2$, O—CO—$CH_2$—$CH_2$-$C_2B_5$, O—CO—$CH(CH_3)$-$C_2H_5$, O—CO—$CH_2$—$CH(CH_3)_2$ or O—CO—$C(CH_3)_3$, preferably O—CO—$CH_3$ or O—CO—$C_2H_5$;

($C_1$-$C_4$-haloalkyl)carbonyloxy: a ($C_1$-$C_4$-alkyl)carbonyl radical as mentioned above which is partially or fully substituted by fluorine, chlorine, bromine and/or iodine, i.e. for example O—CO—$CH_2F$, O—CO—$CHF_2$, O—CO—$CF_3$, O—CO—$CH_2C_1$, O—CO—$CH(C_1)_2$, O—CO—$C(Cl)_3$, chlorofluoro-methylcarbonyloxy, dichlorofluoromethylcarbonyloxy, chlorodifluoromethylcarbonyloxy, 2-fluoroethylcarbonyloxy, 2-chloroethylcarbonyloxy, 2-bromoethylcarbonyloxy, 2-iodoethylcarbonyloxy, 2,2-difluoroethylcarbonyloxy, 2,2,2-trifluoroethylcarbonyloxy, 2-chloro-2-fluoroethyl-carbonyloxy, 2-chloro-2,2-difluoroethylcarbonyloxy, 2,2-dichloro-2-fluoroethylcarbonyloxy, 2,2,2-trichloroethyl-carbonyloxy, O—CO—$C_2F_5$, 2-fluoropropylcarbonyloxy, 3-fluoropropylcarbonyloxy, 2,2-difluoropropylcarbonyloxy, 2,3-difluoropropylcarbonyloxy, 2-chloropropylcarbonyloxy, 3-chloropropylcarbonyloxy, 2,3-dichloropropylcarbonyloxy, 2-bromopropylcarbonyloxy, 3-bromopropylcarbonyloxy, 3,3,3-trifluoropropylcarbonyloxy, 3,3,3-trichloropropyl-carbonyloxy, 2,2,3,3,3-pentafluoropropylcarbonyloxy, heptafluoropropylcarbonyloxy, 1-($CH_2F$)-2-fluoroethyl-carbonyloxy, 1-($CH_2C_1$)-2-chloroethylcarbonyloxy, 1-($CH_2Br$)-2-bromoethylcarbonyloxy, 4-fluorobutylcarbonyloxy, 4-chlorobutylcarbonyloxy, 4-bromobutylcarbonyloxy or nonafluorobutylcarbonyloxy, preferably O—CO—$CF_3$, O—CO—$CH_2C_1$, or 2,2,2-trifluoroethylcarbonyloxy; ($C_1$–$C_4$-alkoxy)carbonyl: CO—$OCH_3$, CO—$OC_2H_5$ n-propoxycarbonyl, CO—$OCH(CH_3)_2$, n-butoxycarbonyl, CO—OCH ($CH_3$) –$C_3H_5$, CO—$OCH_2$—$CH(CH_3)_2$ or CO—OC$(CH_3)_3$ preferably CO—$OCH_3$ or CO-$OC_2B_5$;

($C_1$–$C_4$-alkoxy)carbonyl-$C_1$–$C_4$-alkyl: $C_1$–$C_4$-alkyl which is substituted by ($C_1$–$C_4$-alkoxy)carbonyl as mentioned above, i.e. for example methoxycarbonylmethyl, ethoxycarbonylmethyl, n-propoxycarbonylmethyl, (1-methylethoxycarbonyl)methyl, n-butoxycarbonylmethyl, (1-methylpropoxycarbonyl)methyl, (2-methylpropoxycarbonyl)methyl, (1,1-dimethylethoxy-carbonyl)methyl, 1-(methoxycarbonyl)ethyl, 1-(ethoxy-carbonyl)ethyl, 1-(n-propoxycarbonyl)ethyl, 1-(1-methyl-ethoxycarbonyl)ethyl, 1-(n-butoxycarbonyl)ethyl, 2-(methoxy-carbonyl)ethyl, 2-(ethoxycarbonyl)ethyl, 2-(n-propoxy-carbonyl)ethyl, 2-(1-methylethoxycarbonyl)ethyl, 2-(n-butoxycarbonyl)ethyl, 2-(1-methylpropoxycarbonyl)ethyl, 2-(2-methylpropoxycarbonyl)ethyl, 2-(1,1-dimethylethoxy-carbonyl)ethyl, 2-(methoxycarbonyl)propyl, 2-(ethoxy-carbonyl)propyl, 2-(n-propoxycarbonyl)propyl, 2-(1-methyl-ethoxycarbonyl)propyl, 2-(n-butoxycarbonyl)propyl,2-(1-methylpropoxycarbonyl)propyl, 2-(2-methylpropoxy-carbonyl)propyl, 2-(1,1-dimethylethoxycarbonyl)propyl, 3-(methoxycarbonyl)propyl, 3-(ethoxycarbonyl)propyl, 3-(n-propoxycarbonyl)propyl, 3-(-methylethoxycarbonyl)-propyl, 3-(n-butoxycarbonyl)propyl, 3-(1-methylpropoxy-carbonyl)propyl, 3-(2-methylpropoxycarbonyl)propyl, 3-(1,1-dimethylethoxycarbonyl)propyl, 2-(methoxycarbonyl)-butyl, 2-(ethoxycarbonyl)butyl, 2-(n-propoxycarbonyl)butyl, 2-(1-methylethoxycarbonyl)butyl, 2-(n-butoxycarbonyl)butyl, 2-(1-methylpropoxycarbonyl)butyl, 2-(2-methylpropoxy-carbonyl)butyl, 2-(1,-dimethylethoxycarbonyl)butyl, 3-(methoxycarbonyl)butyl, 3-(ethoxycarbonyl)butyl, 3-(n-propoxycarbonyl)butyl, 3-(1-methylethoxycarbonyl)butyl, 3-(n-butoxycarbonyl)butyl, 3-(1-methylpropoxycarbonyl)butyl, 3-(2-methylpropoxycarbonyl butyl, 3-(1,1-dimethylethoxy-carbonyl)butyl, 4-(methoxycarbonyl)butyl, 4-(ethoxy-carbonyl)butyl, 4-(n-propoxycarbonyl)butyl, 4-(1-methyl-ethoxycarbonyl)butyl, 4-(n-butoxycarbonyl)butyl, 4-(1-methyl-propoxycarbonyl)butyl, 4-(2-methylpropoxycarbonyl)butyl or 4-(1,1-dimethylethoxycarbonyl)butyl, preferably methoxycarbonylmethyl, ethoxycarbonylmethyl, 1-(methoxycarbonyl)ethyl or 1-(ethoxycarbonyl)ethyl;

$C_1$–$C_4$-alkylsulfinyl: SO—$CH_3$, SO—$C_2H_5$, SO—$CH_2$–$C_2H_5$, SO—$CH(CH_3)_2$, n-butylsulfinyl, SO—$CH(CH_3)$–$C_2H_5$, SO—$CH_2$—$CH(C_3)_2$ or SO—C$(CH_3)_3$, preferably SO—$CH_3$ or SO–$C_2H_5$;

$C_1$–$C_4$-haloalkylsulfinyl: a $C_1$–$C_4$-alkylsulfinyl radical as mentioned above which is partially or fully substituted by fluorine, chlorine, bromine and/or iodine, i.e. for example SO—$CH_2F$, SO—$CHF_2$, SO—$CF_3$, SO—$CH_2C_1$, SO—$CH(C_1)_2$, SO—$C(C_1)_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethyl-sulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoro-ethylsulfinyl, 2,2,2-trichloroethylsulfinyl, $SO$–$C_2F_5$, 2-fluoropropylsulfinyl, 3-fluoropropylsulfinyl, 2,2-difluoro-propylsulfinyl, 2,3-difluoropropylsulfinyl, 2-chloropropyl-sulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, SO—$CH_2$–$C_2F_5$, SO—$CF_2$–$C_2F_5$, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutyl-sulfinyl, 4-bromobutylsulfinyl or nonafluorobutylsulfinyl, preferably SO—$CF_3$, SO—$CH_2C_1$or 2,2,2-trifluoroethylsulfinyl;

$C_1$–$C_4$-alkylsulfonyl: $SO_2$—$CH_3$, $SO_2$–$C_2H_5$, $SO_2$—$CH_2$–$C_2H_5$, $SO_2$—$CH(CH_3)_2$, n-butylsulfonyl, $SO_2$—$CH(CH_3)$–$C_2H_5$, $SO_2$—$CH_2$—$CH(CH_3)_2$ or $SO_2$-c$(CH_3)_3$, preferably $SO_2$—$CH_3$ or $SO_2$–$C_2H_5$;

$C_1$–$C_4$-haloalkylsulfonyl: a $C_1$–$C_4$-alkylsulfonyl radical as mentioned above which is partially or fully substituted by fluorine, chlorine, bromine and/or iodine, i.e. for example $SO_2$—$CH_2F$, $SO_2$—$CHF_2$, $SO_2$—$CF_3$, $SO_2$—$CH_2C_1$, $SO_2$—$CH(C_1)_2$r $SO_2$—$C(C_1)_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoro-ethylsulfonyl, 2,2,2-trichloroethylsulfonyl, $SO_2$—$C_2F_5$, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $SO_2$—$CH_2$–$C_2F_5$, $SO_2$—$CF_2$–$C_2F_5$, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl, preferably $SO_2$—$CF_3$, $SO_2$—$CH_2C_1$ or 2,2,2-trifluoroethylsulfonyl;

di($C_1$–$C_4$-alkyl)amino: $N(CH_3)_2$, $N(C_2H_5)$, N,N-dipropylamino, $N[CH(CH_3)_2]_2$, N,N-dibutylamino, N,N-di(1-methylpropyl)amino, N,N-di(2-methylpropyl)amino, $N[C[CH_3)_3]_2$, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl) N-methylamino, N-ethyl-N-propylamino, N-ethyl-N-(1-methyl-ethyl)amino, N-butyl-N-ethylamino, N-ethyl-N-(1-methyl-propyl)amino, N-ethyl-N-(2-methylpropyl)amino, N-ethyl-N-(1,1-dimethylethyl)amino, N-(1-methylethyl)-N-propylamino, N-butyl-N-propylamino, N-(1- methylpropyl)-N-propylamino, N-(2-methylpropyl)-N-propylamino, N-(1,1-dimethylethyl)-N-propylamino, N-butyl-N-(-methylethyl)amino, N-(1-methyl-ethyl)-N-(1-methylpropyl)-amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-

(1,1-dimethyl-ethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, preferably N(CH$_3$)$_2$ or N(C$_2$H$_5$);

$C_2$–$C_6$-alkenyl: vinyl, prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methyl-prop-2-en-1-yl, 2-methyl-prop-2-en-1-yl n-penten-1-yl1 n-penten-2-yl, n-penten-3-yl, n-penten-4-yl, 1-methyl-but-1-en-1-yl, 2-methylbut-1-en-1-yl, 3-methylbut-1-en-1-yl, 1-methylbut-2-en-1-yl, 2-methylbut-2-en-1-yl, 3-methyl-but-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methyl-pent-2-en-1-yl, 4-methylpent-2-en-1-yl, 1-methylpent-3-en- 1-yl, 2-methylpent-3-en-1-yl, 3-methylpent-3-en-1-yl, 4-methylpent-3-en-1-yl, 1-methyl-pent-4-en-1-yl, 2-methyl-pent-4-en-1-yl, 3-methylpent-4-en-1-yl, 4-methylpent-4-en-1-yl, 1$_1$1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, $_{13}$,-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethyl-but-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_2$–$C_6$-haloalkenyl: $C_2$–$C_6$-alkenyl as mentioned above which is partially or fully substituted by fluorine, chlorine and/or bromine, i.e. for example 2-chlorovinyl, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl and 2,3-dibromobut-2-enyl, preferably $C_3$-or $C_4$-haloalkenyl;

$C_2$–$C_6$-alkynyl: ethynyl and $C_3$–$C_6$-alkynyl$_1$ such as prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl1 n-pent-2-yn-5-yl, 3-methylbut-1-yn-3-yl, 3-methylbut-1-yn-4-yl, n-hex-1-yn-1-yl, n-hex-1-yn-3-yl1 n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, preferably prop-2-yn-1-yl;

$C_2$–$C_6$-haloalkynyl: $C_2$–$C_6$-alkynyl as mentioned above which is partially or fully substituted by fluorine, chlorine and/or bromine, i.e. for example 1,1-difluoroprop-2-yn-1-yl, 1,1-difluorobut-2-yn-1-yl, 4-fluorobut-2-in-1-yl, 4-chlorobut-2-yn-1-yl, 5-fluoropent-3-yn-1-yl or 6-fluorohex-4-yn-1-yl, preferably $C_3$- or $C_4$-haloalkynyl;

$C_3$–$C_8$-cycloalkyl: cyclopropyl, cyclobutyl, cyclopentyl, cyclohexyl, cycloheptyl or cyclooctyl;

$C_3$–$C_8$-cycloalkyl containing a carbonyl or thiocarbonyl ring member: for example cyclobutanon-2-yl, cyclobutanon-3-yl, cyclopentanon-2-yl, cyclopentanon-3-yl, cyclohexanon-2-yl, cyclohexanon-4-yl, cycloheptanon-2-yl, cyclooctanon-2-yl, cyclobutanethion-2-yl, cyclobutanethion-3-yl, cyclopentane-thion-2-yl, cyclopentanethion-3-yl, cyclohexanethion-2-yl, cyclohexanethion-4-yl, cycloheptanethion-2-yl or cyclooctanethion-2-yl, preferably cyclopentanon-2-yl or cyclohexanon-2-yl;

$C_3$—CH-cycloalkyl-$C_1$–$C_4$-alkyl: cyclopropylmethyl, 1-cyclo-propylethyl, 2-cyclopropylethyl, 1-cyclopropylprop-1-yl, 2-cyclopropylprop-1-yl, 3-cyclopropylprop-1-yl, 1-cyclo-propylbut-1-yl, 2-cyclopropylbut-1-yl, 3-cyclopropylbut-1-yl, 4-cyclopropylbut-1-yl, 1-cyclopropylbut-2-yl, 2-cyclopropyl-but-2-yl, 3-cyclopropylbut-2-yl, 3-cyclopropylbut-2-yl, 4-cyclopropylbut-2-yl, 1-(cyclopropylmethyl)eth-1-yl, 1-(cyclopropylmethyl)-1-(methyl)eth-1-yl, 1-(cyclopropyl-methyl)prop-1-yl, cyclobutylmethyl, 1-cyclobutylethyl, 2-cyclobutylethyl, 1-cyclobutylprop-1-yl, 2-cyclobutyl-prop-1-yl, 3-cyclobutylprop-1-yl, 1-cyclobutylbut-1-yl, 2-cyclobutylbut-1-yl, 3-cyclobutylbut-1-yl, 4-cyclobutyl-but-1-yl, 1-cyclobutylbut-2-yl, 2-cyclobutylbut-2-yl, 3-cyclobutylbut-2-yl, 3-cyclobutylbut-2-yl, 4-cyclobutyl-but-2-yl, 1-(cyclobutylmethyl)eth-1-yl, 1-(cyclobutyl-methyl)-1-(methyl)eth-1-yl, 1-(cyclobutylmethyl)prop-1-yl, cyclopentylmethyl, 1-cyclopentylethyl, 2-cyclopentylethyl, 1-cyclopentylprop-1-yl, 2-cyclopentylprop-1-yl, 3-cyclopentylprop-1-yl, 1-cyclopentylbut-1-yl, 2-cyclopentylbut-1-yl, 3-cyclopentylbut-1-yl, 4-cyclopentylbut-1-yl, 1-cyclopentylbut-2-yl, 2-cyclopentylbut-2-yl, 3-cyclopentylbut-2-yl, 3-cyclopentylbut-2-yl, 4-cyclopentylbut-2-yl, 1-(cyclopentylmethyl)eth-1-yl, 1-(cyclopentylmethyl)-1-(methyl)eth-1-yl, 1-(cyclopentylmethyl)prop-1-yl, cyclohexylmethyl, 1-cyclohexylethyl, 2-cyclohexylethyl, 1-cyclohexylprop-1-yl, 2-cyclohexylprop-1-yl, 3-cyclohexyl-prop-1-yl, 1-cyclohexylbut-1-yl, 2-cyclohexylbut-1-yl, 3-cyclohexylbut-1-yl, 4-cyclohexylbut-1-yl, 1-cyclohexyl-but-2-yl, 2-cyclohexylbut-2-yl, 3-cyclohexylbut-2-yl, 3-cyclohexylbut-2-yl, 4-cyclohexylbut-2-yl, 1-(cyclohexyl-methyl)eth-1-yl, 1-(cyclchexylmethyl)-1-(methyl)eth-1-yl, 1-(cyclohexylmethyl)prop-1-yl, cycloheptylmethyl, 1-cycloheptylethyl, 2-cycloheptylethyl, 1-cycloheptylprop-1-yl, 2-cycloheptylprop-1-yl, 3-cycloheptylprop-1-yl, 1-cycloheptylbut-1-yl, 2-cycloheptylbut-1-yl, 3-cycloheptyl-but-1-yl, 4-cycloheptylbut-1-yl, 1-cycloheptylbut-2-yl, 2-cycloheptylbut-2-yl, 3-cycloheptyl-but-2-yl, 3-cycloheptyl-but-2-yl, 4-cycloheptylbut-2-yl, 1-(cycloheptylmethyl)eth-1-yl, 1-(cycloheptylmethyl)-1-(methyl)eth-1-yl, 1-(cyclo-heptylmethyl)prop-1-yl, cyclooctylmethyl, 1-cyclooctylethyl, 2-cyclooctylethyl, 1-cyclooctylprop-1-yl, 2-cyclooctyl-prop-1-yl, 3-cyclooctylprop-1-yl, 1-cyclooctylbut-1-yl, 2-cyclooctylbut-1-yl, 3-cyclooctylbut-1-yl, 4-cyclooctyl-but-1-yl, 1-cyclooctylbut-2-yl, 2-cyclooctylbut-2-yl, 3-cyclooctylbut-2-yl, 3-cyclooctylbut-2-yl, 4-cyclooctyl-but-2-yl, 1-(cyclooctylmethyl)eth-1-yl, r 1(cyclooctylmethyl)-1-(methyl)eth-1-yl or 1-(cyclooctylmethyl)prop-1-yl, preferably cyclopropylmethyl, cyclobutylmethyl, cyclopentyl-methyl or cyclohexylmethyl;

$C_3$–$C_8$-cycloalkyl-$C_1$–$C_4$-alkyl containing a carbonyl or thiocarbonyl ring member: for example cyclobutanon-2-yl-methyl, cyclobutanon-3-ylmethyl, cyclopentanon-2-ylmethyl, cyclopentanon-3-ylmethyl, cyclohexanon-2-ylmethyl, cyclohexanon-4-ylmethyl, cycloheptanon-2-ylmethyl, cyclooctanon-2-ylmethyl, cyclobutanethion-2-ylmethyl, cyclobutanethion-3-ylmethyl, cyclopentanethion-2-ylmethyl, cyclopentanethion-3-ylmethyl, cyclohexanethion-2-ylmethyl, cyclohexanethion-4-ylmethyl, cycloheptanethion-2-ylmethyl, cyclooctanethion-2-ylmethyl, 1-(cyclobutanon-2-yl)ethyl, 1-(cyclobutanon-3-yl)ethyl, 1-(cyclopentanon-2-yl) ethyl, (cyclopentanon-3-yl)ethyl, 1-(cyclohexanon-2-yl)ethyl, 1-(cyclohexanon-4-yl)ethyl, 1-(cycloheptanon-2-yl)ethyl, 1-(cyclooctanon-2-yl) ethyl, 1-(cyclobutanethion-2-yl)ethyl, 1-(cyclobutanethion-3-yl)ethyl, 1-(cyclopentanethion-2-yl)-ethyl, 1-(cyclopentanethion-3-yl)ethyl, 1-(cyclohexane-thion-2-yl) ethyl, 1-(cyclohexanethion-4-yl)ethyl, 1-(cycloheptanethion-2-yl)ethyl, 1-(cyclooctanethion-2-yl) ethyl, 2-(cyclobutanon-2-yl)ethyl, 2-(cyclobutanon-3-yl)ethyl, 2-(cyclopentanon-2-yl)ethyl, 2-(cyclopentanon-3-yl)ethyl, 2-(cyclohexanon-2-yl) ethyl, 2-(cyclohexanon-4-yl)ethyl, 2-(cycloheptanon-2-yl)ethyl, 2-(cyclooctanon-2-yl)ethyl, 2-(cyclobutanethion-2-yl)ethyl, 2-(cyclobutanethion-3-yl)ethyl, 2-(cyclopentanethion-2-yl)ethyl, 2-(cyclopentanethion-3-yl)-ethyl, 2-(cyclohexanethion-2-yl) ethyl, 2-(cyclohexanethion-4-yl) ethyl, 2-(cycloheptanethion-2-yl)ethyl, 2-(cyclooctanethion-2-yl)ethyl, 3-(cyclobutanon-2-yl) propyl, 3-(cyclobutanon-3-yl)propyl, 3-(cyclopentanon-2-yl)propyl, 3-(cyclopentanon-3-yl) propyl, 3-(cyclohexanon-2-yl)propyl, 3-(cyclohexanon-4-yl)propyl, 3-(cycloheptanon-2-yl) propyl, 3-(cyclooctanon-2-yl)propyl, 3-(cyclobutanethion-2-yl)propyl, 3-(cyclobutanethion-3-yl)propyl, 3-(cyclopentanethion-2-yl)-propyl, 3-(cyclopentanethion-3-yl)propyl, 3-(cyclohexane-thion-2-yl) propyl, 3-(cyclohexanethion-4-yl)propyl, 3-(cyclo-heptanethion-2-yl) propyl, 3-(cyclooctanethion-2-yl)propyl, 4-(cyclobutanon-2-yl)butyl, 4-(cyclobutanon-3-yl)butyl, 4-(cyclopentanon-2-yl)butyl, 4-(cyclopentanon-3-yl) butyl, 4-(cyclohexanon-2-yl)butyl, 4-(cyclohexanon-4-yl)butyl, 4-(cycloheptanon-2-yl)butyl, 4-(cyclooctanon-2-yl)butyl, 4-(cyclobutanethion-2-yl) butyl, 4-(cyclobutanethion-3-yl)-butyl, 4-(cyclopentanethion-2-yl)butyl, 4-(cyclopentanethion-3-yl)butyl, 4-(cyclohexanethion-2-yl)butyl, 4-(cyclo-hexanethion-4-yl)butyl, 4-(cycloheptanethion-2-yl)butyl or 4-(cyclooctanethion-2-yl)butyl, preferably cyclopentanon-2-ylmethyl, cyclohexanon-2-ylmethyl, 2-(cyclopenta-non-2-yl)ethyl or 2-(cyclohexanon-2-yl)ethyl.

3- to 7-membered heterocyclyl is a saturated, partially or fully unsaturated or aromatic heterocycle having one to three hetero atoms selected from a group consisting of one to three nitrogens,
one or two oxygens and
one or two sulfur atoms.

Examples of saturated heterocycles containing a carbonyl or thiocarbonyl ring member are:

oxiranyl, thiiranyl, aziridin-1-yl, aziridin-2-yl, diaziridin-1-yl, diaziridin-3-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-2-yl, 1,3-dithiepan-2-yl, 1, 3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl.

Examples of unsaturated heterocycles containing a carbonyl or thiocarbonyl ring member are: dihydrofuran-2-yl, 1,2-oxazolin-3-yl, 1,2-oxazolin-5-yl, 1,3-oxazolin-2-yl.

Preferred heteroaromatics are the 5- and 6-membered heteroaromatics, i.e. for example, furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 112,4-triazol-3-yl and 112,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, and furthermore 2-pyrazinyl, 1,3,5-triazin-2-yl and 1,2,4-triazin-3-yl, in particular pyridyl, pyrimidyl, furanyl and thienyl.

All phenyl, carbocyclic and heterocyclic rings are preferably unsubstituted or carry one substituent.

Preferred with a view to the use of the 1-sulfonyl-3-phenyl-pyrazoles I as herbicides or desiccants/defoliants are those compounds I where the substituents have the following meanings, in each case either on their own or in combination:

$R^1$ is methyl, ethyl or $C_1$–$C_2$-haloalkyl, in particular methyl;
$R^2$ is methyl, ethyl or $C_1$–$C_2$-haloalkyl, in particular methyl;
$R^3$ is hydrogen or halogen, in particular halogen, particularly preferably chlorine;
$R^4$ is hydrogen, fluorine or chlorine, in particular fluorine, particularly preferably fluorine;
X is a chemical bond or a methylene or ethene-1,2-diyl chain or an oxymethylene or thiamethylene chain linked to the phenyl ring via the hetero atom, the chains being in each case unsubstituted or substituted by a cyano, halogen, $C_1$–$C_4$-alkyl or ($C_1$–$C_4$-alkoxy)carbonyl substituent, in particular a chemical bond or methylene;
$R^6$ is hydrogen, —O—Y—$R^8$, —O—CO—Y—Re, —N(Y—Re)—$SO_2$—Z—$R^9$, —N($SO_2$—Y—$R^8$)($SO_2$—Z—$R^9$), —S—Y—Re, —$SO_2$—N(Y—$R^3$)(Z—$R^9$), —$C_1$(=$NOR^{10}$)—O—Y—$R^8$, —C—O—Y—$R^6$, —C—N(Y—$R^8$)(Z—$R^9$) or —PO(O—Y—$R,^3$)$_2$, in particular hyrogen, —O—Y—Re, —N(Y—Ra)—$SO_2$—Z—$R^9$, —S—Y—$R^8$ or —CO—OY—$R_8$, particularly preferably hydrogen or —O—Y—$R^8$,
$R^7$ is hydrogen;
or $R^5$ and $XR^6$ or $XR^6$ and $R^7$ form together with the carbons of the phenyl ring linking them a fused heterocyclic ring selected from the group consisting of furan, dihydrofuran, thiophene, dihydrothiophene, pyrrole, dibydropyrrole, 1,3-dioxolane, 1,3-dioxolan-2-one, isoxazole, oxazole, oxazolinone, isothiazole, thiazole, pyrazole, pyrazoline, imidazole, imidazolinone, dihydroimidazole, 1,2,3-triazole, 1,1-dioxo-dihydroisothiazole, dihydro-1,4-dioxin, pyridone, dihydro-1,4-oxazine, dihydro-1,4-oxazin-2-one, dihydro-1,4-oxazin-3-one, dihydro-1,3-oxazine and dihydro-1,3-oxazin-2-one, the fused ring being unsubstituted or substituted by one or two substituents selected in each case from the group consisting of $C_1$–$C_4$-alkyl, $C_1$–$C_4$-haloalkyl, $C_3$–$C_4$-alkenyl, $C_3$–$C_4$-haloalkenyl, $C_3$–$C_4$-alkynyl and $C_1$–$C_4$-alkoxy;
Y and Z are each independently of each other a chemical bond or methylene;
$R^8$ and $R^9$ are independently of each other hydrogen, $C_1$–$C_6$-haloalkyl, $C_2$–$C_6$-alkenyl, $C_2$–$C_6$-haloalkenyl, $C_2$–$C_6$-alkynyl, —CH($R^{11}$)($R^{12}$), —C($R^{11}$)($R^{12}$)—$NO_2$, —C($R^{13}$)($R^{12}$)—CN, —C($R^{11}$)($R^{12}$)-halogen, —C($R^{11}$)($R^{12}$)—$OR^{13}$, —C($R^{11}$)($R^{12}$)—N($R^{13}$)$R^{14}$, —C($R^{11}$)($R^{12}$)—N($R^{13}$)—$OR^{14}$, —C($R^{11}$)($R^{12}$)—$SR^{13}$, —C($R^{11}$)($R^{12}$)—SO—$R^{13}$, —C($R^{11}$)($R^{12}$)—$SO_2$—$R^{13}$, —C($R^{11}$)($R^{12}$)—$SO_2$—$OR^{13}$, —C($R^{11}$)($R^{12}$)—$SO_2$—N($R^{13}$)$R^{14}$, —C($R^{11}$)($R^{12}$)—CO—$R^{13}$, —C($R^{11}$)($R^{12}$)—C(=$NOR^{15}$)—$R^{13}$, —C($R^{11}$)($R^{12}$)—$COOR^{13}$, —C($R^{11}$)($R^{12}$)—CO-$SR^{13}$, —C($R^{11}$)($R^{12}$)—CO—N($R^{13}$)$R^{14}$, —C($R^{11}$)($R^{12}$)—CON($R^{13}$)—$OR^{14}$, $C_3$–$C_8$-cycloalkyl which may contain a carbonyl or thiocarbonyl ring member, phenyl or 3- to 7-membered heterocyclyl having one or two nitrogens and/or one oxygen or sulfur atom as hetero atom and, if desired, a carbonyl or thiocarbonyl ring member, the cycloalkyl, phenyl and heterocyclyl rings being in each case unsubstituted or substituted by one or two substituents selected in each case from the group consisting of cyano, nitro, halogen, $C_1$–$C_4$-alkyl, $C_1$–$C_4$-alkoxy, $C_1$–$C_4$-alkylsulfonyl, ($C_1$–$C_4$-alkyl) carbonyl, ($C_1$–$C_4$-alkyl)-carbonyloxy and ($C_1$–$C_4$-alkoxy)carbonyl; in particular hydrogen, $C_1$–$C_6$-alkyl, $C_1$–$C_6$-haloalkyl, $C_2$–$C_6$-alkenyl, $C_2$–$C_6$-alkynyl, —CH($R^{11}$)($R^{12}$), —C($R^{11}$)($R^{12}$)—CO-$OR^{13}$, —C($R^{11}$)($R^{12}$)—CO—N($R^{13}$)$R^{14}$ or $C_3$—CO-cycloalkyl, particularly preferably hydrogen, $C_1$–$C_6$-alkyl, $C_2$–$C_6$-alkenyl, $C_2$–$C_6$-alkynyl, —C($R^{11}$)($R^{12}$)—CO—$OR^{13}$ or $C_3$–$C_8$-cycloalkyl;
$R^{10}$ is $C_1$–$C_6$-alkyl;
$R^{11}$ is hydrogen or $C_1$–$C_4$-alkyl;
$R^{12}$ is hydrogen;
$R^{13}$ and $R^{14}$ are each independently of each other hydrogen or $C_1$–$C_6$-alkyl;
$R^{15}$ is $C_1$–$C_6$-alkyl.

Particular preference is further given to those 1-sulfonyl-3-phenylpyrazoles I in which X is a chemical bond or methylene and $R^7$ is hydrogen.

Very particular preference is given to the compounds Ia (= with $R^1$ and $R^2$=methyl; $R^3$, $R^4$ and $R^7$=hydrogen; $R^8$=chlorine) listed in Table 1 below:

TABLE 1

Ia

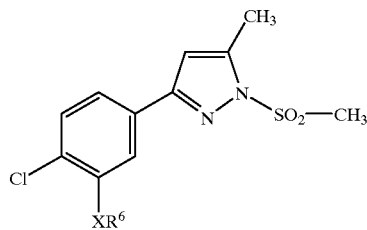

| No. | —$XR^6$ |
|---|---|
| Ia.001 | —H |
| Ia.002 | —$CH_3$ |
| Ia.003 | —$NO_2$ |
| Ia.004 | —CN |
| Ia.005 | —F |
| Ia.006 | —Cl |
| Ia.007 | —Br |
| Ia.008 | —OH |
| Ia.009 | —$OCH_3$ |
| Ia.010 | —$OC_2H_5$ |
| Ia.011 | —O(n-$C_3H_7$) |
| Ia.012 | —$OCH(CH_3)_2$ |
| Ia.013 | —O(n-$C_4H_9$) |
| Ia.014 | —$OCH_2$—$CH(CH_3)_2$ |
| Ia.015 | —$OCH(CH_3)$—$C_2H_5$ |
| Ia.016 | —$OC(CH_3)_3$ |
| Ia.017 | —$OCH_2$—CH=$CH_2$ |
| Ia.018 | —$OCH_2$—CH=CH-$CH_3$ |
| Ia.019 | —$OCH_2$—$CH_2$—CH=$CH_2$ |
| Ia.020 | —$OCH(CH_3)$—CH=$CH_2$ |
| Ia.021 | —$OCH_2$—C≡CH |
| Ia.022 | —$OCH(CH_3)$—C≡CH |
| Ia.023 | —$OCH_2$—$OCH_3$ |
| Ia.024 | —$OCH_2$—$CH_2$—$OCH_3$ |
| Ia.025 | —$OCH_2$—CN |
| Ia.026 | —$OCH_2$—$CH_2$F |
| Ia.027 | —$OCH_2$—$CF_3$ |
| Ia.028 | —$OCH_2$—$CH_2$Cl |
| Ia.029 | —$OCH_2$—CO—$OCH_3$ |
| Ia.030 | —$OCH_2$—CO—$OC_2H_5$ |
| Ia.031 | —$OCH_2$—CO—N($CH_3$)$_2$ |
| Ia.032 | —$OCH(CH_3)$—CO—$OCH_3$ |
| Ia.033 | —$OCH(CH_3)$—CO—$OC_2H_5$ |
| Ia.034 | —$OCH(CH_3)$—CO—N($CH_3$)$_2$ |
| Ia.035 | —O-cyclobutyl |
| Ia.036 | —O-cyclopentyl |
| Ia.037 | —O-cyclohexyl |
| Ia.038 | —$OCH_2$-cyclobutyl |
| Ia.039 | —$OCH_2$-cyclopentyl |
| Ia.040 | —$OCH_2$-cyclohexyl |
| Ia.041 | —$OCH_2$-phenyl |
| Ia.042 | —O—CO—$CH_3$ |

TABLE 1-continued

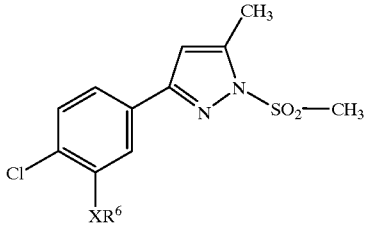

| No. | —XR⁶ |
|---|---|
| Ia.043 | —O—CO—$C_2H_5$ |
| Ia.044 | —O—CO-(n-$C_3H_7$) |
| Ia.045 | —O—CO-(n-$C_4H_9$) |
| Ia.046 | —O—CO—CH($CH_3$)$_2$ |
| Ia.047 | —O—CO—$CH_2$—CH($CH_3$)$_2$ |
| Ia.048 | —O—CO—CH($CH_3$)—$C_2H_5$ |
| Ia.049 | —O—CO—C($CH_3$)$_3$ |
| Ia.050 | —O—CO—$CH_2$Cl |
| Ia.051 | —O—CO—$CH_2$—$OCH_3$ |
| Ia.052 | —O—CO-cyclobutyl |
| Ia.053 | —O—CO-cyclopentyl |
| Ia.054 | —O—CO-cyclohexyl |
| Ia.055 | —O—CO-phenyl |
| Ia.056 | —$CH_2$—OH |
| Ia.057 | —$CH_2$—$OCH_3$ |
| Ia.058 | —$CH_2$—$OCH_2$—CO—$OCH_3$ |
| Ia.059 | —$CH_2$—O—CO—$CH_3$ |
| Ia.060 | —$CH_2$—O-cyclopentyl |
| Ia.061 | —$CH_2$—$OCH_2$-phenyl |
| Ia.062 | —$NH_2$ |
| Ia.063 | —NH—$CH_3$ |
| Ia.064 | —N($CH_3$)$_2$ |
| Ia.065 | —NH—$C_2H_5$ |
| Ia.066 | —N($C_2H_5$)$_2$ |
| Ia.067 | —NH-(n-$C_3H_7$) |
| Ia.068 | —N(n-$C_3H_7$)$_2$ |
| Ia.069 | —NH-(n-$C_4H_9$) |
| Ia.070 | —N(n-$C_4H_9$)$_2$ |
| Ia.071 | —NH—CH($CH_3$)$_2$ |
| Ia.072 | —N[CH($CH_3$)$_2$]$_2$ |
| Ia.073 | —NH—$CH_2$—CH($CH_3$)$_2$ |
| Ia.074 | —N[$CH_2$—CH($CH_3$)$_2$]$_2$ |
| Ia.075 | —NH—$CH_2$—CH═$CH_2$ |
| Ia.076 | —N($CH_2$—CH═$CH_2$)$_2$ |
| Ia.077 | —NH—$CH_2$—C≡CH |
| Ia.078 | —N($CH_2$—C≡CH)$_2$ |
| Ia.079 | —NH—CO—$CH_3$ |
| Ia.080 | —NH—CO—$C_2H_5$ |
| Ia.081 | —NH—CO-(n-$C_3H_7$) |
| Ia.082 | —NH—CO-(n-$C_4H_9$) |
| Ia.083 | —NH—CO—CH($CH_3$)$_2$ |
| Ia.084 | —NH—CO—$CH_2$—CH($CH_3$)$_2$ |
| Ia.085 | —NH—CO—CH($CH_3$)—$C_2H_5$ |
| Ia.086 | —NH—CO—C($CH_3$)$_3$ |
| Ia.087 | —NH—CO—$CH_2$Cl |
| Ia.088 | —NH—CO—$CH_2$—$OCH_3$ |
| Ia.089 | —NH—CO-cyclobutyl |
| Ia.090 | —NH—CO-cyclopentyl |
| Ia.091 | —NH—CO-cyclohexyl |
| Ia.092 | —NH—CO-phenyl |
| Ia.093 | —N($SO_2$—$CH_3$)$_2$ |
| Ia.094 | —NH—$SO_2$—$CH_3$ |
| Ia.095 | —N($SO_2$—$C_2H_5$)$_2$ |
| Ia.096 | —NH—$SO_2$—$C_2H_5$ |
| Ia.097 | —N[$SO_2$-(n-$C_3H_7$)]$_2$ |
| Ia.098 | —NH—$SO_2$-(n-$C_3H_7$) |
| Ia.099 | —N[$SO_2$-(n-$C_4H_9$)]$_2$ |
| Ia.100 | —NH—$SO_2$-(n-$C_4H_9$) |
| Ia.101 | —N[$SO_2$—CH($CH_3$)$_2$]$_2$ |
| Ia.102 | —NH—$SO_2$—CH($CH_3$)$_2$ |
| Ia.103 | —N[$SO_2$—$CH_2$—CH($CH_3$)$_2$]$_2$ |
| Ia.104 | —NH—$SO_2$—$CH_2$—CH($CH_3$)$_2$ |
| Ia.105 | —N($SO_2$—$CH_2$Cl)$_2$ |

TABLE 1-continued

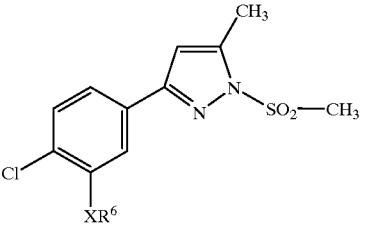

| No. | —XR⁶ |
|---|---|
| Ia.106 | —NH—$SO_2$—$CH_2$Cl |
| Ia.107 | —N($SO_2$—$CH_2$Cl)$_2$ |
| Ia.108 | —NH—$SO_2$—$CH_2$Cl |
| Ia.109 | —N($SO_2$-phenyl)$_2$ |
| Ia.110 | —NH—$SO_2$-phenyl |
| Ia.111 | —N($SO_2$—$CH_2$-phenyl)$_2$ |
| Ia.112 | —NH—$SO_2$—$CH_2$-phenyl |
| Ia.113 | —$CH_2$-N($CH_3$)$_2$ |
| Ia.114 | —$CH_2$-NH—$CH_2$—CO—$OCH_3$ |
| Ia.115 | —NH—OH |
| Ia.116 | —N($CH_3$)-$OCH_3$ |
| Ia.117 | —$CH_2$-NH-OH |
| Ia.118 | —$CH_2$-N($CH_3$)-$OCH_3$ |
| Ia.119 | —SH |
| Ia.120 | —$SCH_3$ |
| Ia.121 | —$SC_2H_5$ |
| Ia.122 | —S-(n-$C_3H_7$) |
| Ia.123 | —S-(n-$C_4H_9$) |
| Ia.124 | —SCH($CH_3$)$_2$ |
| Ia.125 | —$SCH_2$—CH($CH_3$)$_2$ |
| Ia.126 | —SCH($CH_3$)—$C_2H_5$ |
| Ia.127 | —SC($CH_3$)$_3$ |
| Ia.128 | —$SCH_2$—CH═$CH_2$ |
| Ia.129 | —$SCH_2$—CH═CH—$CH_3$ |
| Ia.130 | —$SCH_2$—$CH_2$—CH═$CH_2$ |
| Ia.131 | —SCH($CH_3$)—CH═$CH_2$ |
| Ia.132 | —$SCH_2$—C≡H |
| Ia.133 | —SCH($CH_3$)—C≡CH |
| Ia.134 | —$SCH_2$—$OCH_3$ |
| Ia.135 | —$SCH_2$—$CH_2$—$OCH_3$ |
| Ia.136 | —$SCH_2$—CN |
| Ia.137 | —$SCH_2$—$CH_2$F |
| Ia.138 | —$SCH_2$—$CF_3$ |
| Ia.139 | —$SCH_2$—$CH_2$Cl |
| Ia.140 | —$SCH_2$—CO—$OCH_3$ |
| Ia.141 | —$SCH_2$—CO—$OC_2H_5$ |
| Ia.142 | —$SCH_2$—CO—N($CH_3$)$_2$ |
| Ia.143 | —SCH($CH_3$)—CO—$OCH_3$ |
| Ia.144 | —SCH($CH_3$)—CO—$OC_2H_5$ |
| Ia.145 | —SCH($CH_3$)—CO—N($CH_3$)$_2$ |
| Ia.146 | —S-cyclobutyl |
| Ia.147 | —S-cyclopentyl |
| Ia.148 | —S-cyclohexyl |
| Ia.149 | —$SCH_2$-cyclobutyl |
| Ia.150 | —$SCH_2$-cyclopentyl |
| Ia.151 | —$SCH_2$-cyclohexyl |
| Ia.152 | —$SCH_2$-phenyl |
| Ia.153 | —S—CO—$CH_3$ |
| Ia.154 | —S—CO—$C_2H_5$ |
| Ia.155 | —S—CO-(n-$C_3H_7$) |
| Ia.156 | —S—CO-(n-$C_4H_9$) |
| Ia.157 | —S—CO—CH($CH_3$)$_2$ |
| Ia.158 | —S—CO—$CH_2$—CH($CH_3$)$_2$ |
| Ia.159 | —S—CO—CH($CH_3$)—$C_2H_5$ |
| Ia.160 | —S—CO—C($CH_3$)$_3$ |
| Ia.161 | —S—CO—$CH_2$Cl |
| Ia.162 | —S—CO—$CH_2$—$OCH_3$ |
| Ia.163 | —S—CO-cyclobutyl |
| Ia.164 | —S—CO-cyclopentyl |
| Ia.165 | —S—CO-cyclohexyl |
| Ia.166 | —S—CO-phenyl |
| Ia.167 | —$CH_2$-$SCH_3$ |
| Ia.168 | —SO—$CH_3$ |

TABLE 1-continued

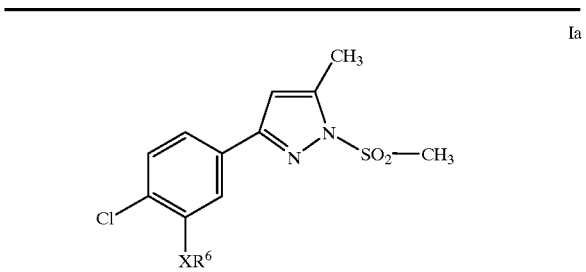

| No. | —XR⁶ |
|---|---|
| Ia.169 | —SO—C$_2$H$_5$ |
| Ia.170 | —SO-(n-C$_3$H$_7$) |
| Ia.171 | —SO-(n-C$_4$H$_9$) |
| Ia.172 | —SO—CH(CH$_3$)$_2$ |
| Ia.173 | —SO—CH$_2$—CH(CH$_3$)$_2$ |
| Ia.174 | —SO—CH(CH$_3$)—C$_2$H$_5$ |
| Ia.175 | —SO—C(CH$_3$)$_3$ |
| Ia.176 | —SO—CH$_2$—CH=CH$_2$ |
| Ia.177 | —SO—CH$_2$—C≡CH |
| Ia.178 | —SO$_2$—CH$_3$ |
| Ia.179 | —SO$_2$—C$_2$H$_5$ |
| Ia.180 | —SO$_2$-(n-C$_3$H$_7$) |
| Ia.181 | —SO$_2$-(n-C$_4$H$_9$) |
| Ia.182 | —SO$_2$—CH(CH$_3$)$_2$ |
| Ia.183 | —SO$_2$—CH$_2$—CH(CH$_3$)$_2$ |
| Ia.184 | —SO$_2$—CH(CH$_3$)—C$_2$H$_5$ |
| Ia.185 | —SO$_2$—C(CH$_3$)$_3$ |
| Ia.186 | —SO$_2$—CH$_2$—CH=CH$_2$ |
| Ia.187 | —SO$_2$—CH$_2$—C≡CH |
| Ia.188 | —SO$_2$—OH |
| Ia.189 | —SO$_2$—OCH$_3$ |
| Ia.190 | —SO$_2$—OC$_2$H$_5$ |
| Ia.191 | —SO$_2$—O(n-C$_3$H$_7$) |
| Ia.192 | —SO$_2$—O(n-C$_4$H$_9$) |
| Ia.193 | —SO$_2$—OCH(CH$_3$)$_2$ |
| Ia.194 | —SO$_2$—OCH$_2$—CH(CH$_3$)$_2$ |
| Ia.195 | —SO$_2$—OCH(CH$_3$)—C$_2$H$_5$ |
| Ia.196 | —SO$_2$—OC(CH$_3$)$_3$ |
| Ia.197 | —SO$_2$—OCH$_2$—CH=CH$_2$ |
| Ia.198 | —SO$_2$—OCH$_2$—C≡CH |
| Ia.199 | —SO$_2$—O-cyclobutyl |
| Ia.200 | —SO$_2$—O-cyclopentyl |
| Ia.201 | —SO$_2$—O-cyclohexyl |
| Ia.202 | —SO$_2$—O-phenyl |
| Ia.203 | —SO$_2$—OCH$_2$-phenyl |
| Ia.204 | —SO$_2$-NH$_2$ |
| Ia.205 | —SO$_2$-NH—CH$_3$ |
| Ia.206 | —SO$_2$-N(CH$_3$)$_2$ |
| Ia.207 | —SO$_2$-NH—C$_2$H$_5$ |
| Ia.208 | —SO$_2$-N(C$_2$H$_5$)$_2$ |
| Ia.209 | —SO$_2$-NH-(n-C$_3$H$_7$) |
| Ia.210 | —SO$_2$-N(n-C$_3$H$_7$)$_2$ |
| Ia.211 | —SO$_2$-NH-(n-C$_4$H$_9$) |
| Ia.212 | —SO$_2$-N(n-C$_4$H$_9$)$_2$ |
| Ia.213 | —SO$_2$-NH—CH$_2$—CO—OCH$_3$ |
| Ia.214 | —SO$_2$-NH—CH$_2$—CO—OC$_2$H$_5$ |
| Ia.215 | —SO$_2$-N(CH$_3$)—CH$_2$—CO—OCH$_3$ |
| Ia.216 | —SO$_2$-N(CH$_3$)—CH$_2$—CO—OC$_2$H$_5$ |
| Ia.217 | —SO$_2$-NH-cyclobutyl |
| Ia.218 | —SO$_2$-NH-cyclopentyl |
| Ia.219 | —SO$_2$-NH-cyclohexyl |
| Ia.220 | —SO$_2$-NH-phenyl |
| Ia.221 | —SO$_2$-NH—CH$_2$-phenyl |
| Ia.222 | —SO$_2$-(pyrrolidin-1-yl) |
| Ia.223 | —SO$_2$-(piperidin-1-yl) |
| Ia.224 | —SO$_2$-(2-methoxycarbonylpyrrolidin-1-yl) |
| Ia.225 | —SO$_2$-(2-methoxycarbonylpiperidin-1-yl) |
| Ia.226 | —CHO |
| Ia.227 | —CO—CH$_3$ |
| Ia.228 | —CO—C$_2$H$_5$ |
| Ia.229 | —CO-(n-C$_3$H$_7$) |
| Ia.230 | —CO-(n-C$_4$H$_9$) |
| Ia.231 | —CO—CH(CH$_3$)$_2$ |
| Ia.232 | —CO—CH$_2$—CH(CH$_3$)$_2$ |
| Ia.233 | —CO—CH(CH$_3$)—C$_2$H$_5$ |
| Ia.234 | —CO—C(CH$_3$)$_3$ |
| Ia.235 | —CO—CH$_2$Cl |
| Ia.236 | —CO-cyclobutyl |
| Ia.237 | —CO-cyclopentyl |
| Ia.238 | —CO-cyclohexyl |
| Ia.239 | —CO-phenyl |
| Ia.240 | —CH(=N—OH) |
| Ia.241 | —CH(=N—OCH$_3$) |
| Ia.242 | —CH(=N—OC$_2$H$_5$) |
| Ia.243 | —CH[=N—O(n-C$_3$H$_7$)] |
| Ia.244 | —CH[=N—O(n-C$_4$H$_9$)] |
| Ia.245 | —CH[=N—OCH(CH$_3$)$_2$] |
| Ia.246 | —CH[=N—OCH$_2$—CH(CH$_3$)$_2$] |
| Ia.247 | —CH[=N—OCH(CH$_3$)—C$_2$H$_5$] |
| Ia.248 | —CH[=N—OC(CH$_3$)$_3$] |
| Ia.249 | —CH(=N—OCH$_2$—OCH$_3$) |
| Ia.250 | —CH(=N—O-cyclobutyl) |
| Ia.251 | —CH(=N—O-cyclopentyl) |
| Ia.252 | —CH(=N—O-cyclohexyl) |
| Ia.253 | —CH(=N—O-phenyl) |
| Ia.254 | —CH(=N—OCH$_2$-phenyl) |
| Ia.255 | —CO—OH |
| Ia.256 | —CO—OCH$_3$ |
| Ia.257 | —CO—OC$_2$H$_5$ |
| Ia.258 | —CO—O-(n-C$_3$H$_7$) |
| Ia.259 | —CO—OCH(CH$_3$)$_2$ |
| Ia.260 | —CO—O-(n-C$_4$H$_9$) |
| Ia.261 | —CO—OCH$_2$—CH(CH$_3$)$_2$ |
| Ia.262 | —CO—OCH(CH$_3$)—C$_2$H$_5$ |
| Ia.263 | —CO—OC(CH$_3$)$_3$ |
| Ia.264 | —CO—OCH$_2$—CH=CH$_2$ |
| Ia.265 | —CO—OCH$_2$—CH=CH—CH$_3$ |
| Ia.266 | —CO—OCH$_2$—CH$_2$—CH=CH$_2$ |
| Ia.267 | —CO—OCH(CH$_3$)—CH=CH$_2$ |
| Ia.268 | —CO—OCH$_2$—C≡CH |
| Ia.269 | —CO—OCH(CH$_3$)—C≡CH |
| Ia.270 | —CO—OCH$_2$—CH$_2$—OCH$_3$ |
| Ia.271 | —CO—OCH$_2$—CN |
| Ia.272 | —CO—OCH$_2$—CH$_2$F |
| Ia.273 | —CO—OCH$_2$—CF$_3$ |
| Ia.274 | —CO—OCH$_2$—CH$_2$Cl |
| Ia.275 | —CO—O-cyclobutyl |
| Ia.276 | —CO—O-cyclopentyl |
| Ia.277 | —CO—O-cyclohexyl |
| Ia.278 | —CO—O-phenyl |
| Ia.279 | —CO—O-(3-acetoxytetrahydrofuran-4-yl) |
| Ia.280 | —CO—OCH$_2$-cyclobutyl |
| Ia.281 | —CO—OCH$_2$-cyclopentyl |
| Ia.282 | —CO—OCH$_2$-cyclohexyl |
| Ia.283 | —CO—OCH$_2$-phenyl |
| Ia.284 | —CO—OCH$_2$-(2-oxiranyl) |
| Ia.285 | —CO—OCH$_2$-(morpholin-4-yl) |
| Ia.286 | —CO—OCH$_2$—CO—OCH$_3$ |
| Ia.287 | —CO—OCH$_2$—CO—OC$_2$H$_5$ |
| Ia.288 | —CO—OCH$_2$—CO—N(CH$_3$)$_2$ |
| Ia.289 | —CO—OCH(CH$_3$)—CO—OCH$_3$ |
| Ia.290 | —CO—OCH(CH$_3$)—CO—OC$_2$H$_5$ |
| Ia.291 | —CO—OCH(CH$_3$)—CO—N(CH$_3$)$_2$ |
| Ia.292 | —CH$_2$—CH(Cl)—CO—OH |
| Ia.293 | —CH$_2$—CH(Cl)—CO—OCH$_3$ |
| Ia.294 | —CH$_2$—CH(Cl)—CO—OC$_2$H$_5$ |

TABLE 1-continued

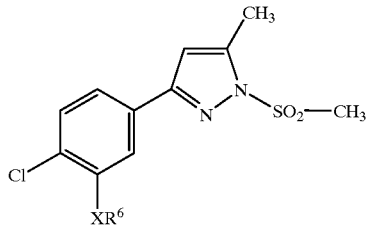

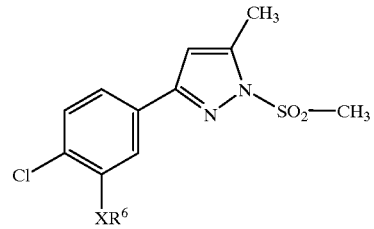

| No. | —XR⁶ |
|---|---|
| Ia.295 | —CH₂—CH(Cl)—CO—O(n-C₃H₇) |
| Ia.296 | —CH₂—CH(Cl)—CO—O(n-C₄H₉) |
| Ia.297 | —CH₂—CH(Cl)—CO—OCH(CH₃)₂ |
| Ia.298 | —CH₂—CH(Cl)—CO—OCH₂—CH(CH₃)₂ |
| Ia.299 | —CH₂—CH(Cl)—CO—OCH(CH₃)—C₂H₅ |
| Ia.300 | —CH₂—CH(Cl)—CO—OC(CH₃)₃ |
| Ia.301 | —CH₂—CH(Cl)—CO—OCH₂—CH=CH₂ |
| Ia.302 | —CH₂—CH(Cl)—CO—OCH₂—C≡CH |
| Ia.303 | —CH₂—CH(Cl)—CO—OCH₂—CO—OCH₃ |
| Ia.304 | —CH₂—CH(Cl)—CO—OCH₂—CO—OC₂H₅ |
| Ia.305 | —CH₂—CH(Cl)—CO—OCH₂—CO—N(CH₃)₂ |
| Ia.306 | —CH₂—CH(Cl)—CO—OCH(CH₃)—CO—OCH₃ |
| Ia.307 | —CH₂—CH(Cl)—CO—OCH(CH₃)—CO—OC₂H₅ |
| Ia.308 | —CH₂—CH(Cl)—CO—OCH(CH₃)—CO—N(CH₃)₂ |
| Ia.309 | —CH₂—CH(Br)—CO—OH |
| Ia.310 | —CH₂—CH(Br)—CO—OCH₃ |
| Ia.311 | —CH₂—CH(Br)—CO—OC₂H₅ |
| Ia.312 | —CH₂—CH(Br)—CO—O(n-C₃H₇) |
| Ia.313 | —CH₂—CH(Br)—CO—O(n-C₄H₉) |
| Ia.314 | —CH₂—CH(Br)—CO—OCH(CH₃)₂ |
| Ia.315 | —CH₂—CH(Br)—CO—OCH₂—CH(CH₃)₂ |
| Ia.316 | —CH₂—CH(Br)—CO—OCH(CH₃)—C₂H₅ |
| Ia.317 | —CH₂—CH(Br)—CO—OC(CH₃)₃ |
| Ia.318 | —CH₂—CH(Br)—CO—OCH₂—CH=CH₂ |
| Ia.319 | —CH₂—CH(Br)—CO—OCH₂—C≡CH |
| Ia.320 | —CH₂—CH(Br)—CO—OCH₂—CO—OCH₃ |
| Ia.321 | —CH₂—CH(Br)—CO—OCH₂—CO—OC₂H₅ |
| Ia.322 | —CH₂—CH(Br)—CO—OCH₂—CO—N(CH₃)₂ |
| Ia.323 | —CH₂—CH(Br)—CO—OCH(CH₃)—CO—OCH₃ |
| Ia.324 | —CH₂—CH(Br)—CO—OCH(CH₃)—CO—OC₂H₅ |
| Ia.325 | —CH₂—CH(Br)—CO—OCH(CH₃)—CO—N(CH₃)₂ |
| Ia.326 | —CH₂—CH(CN)—CO—OH |
| Ia.327 | —CH₂—CH(CN)—CO—OCH₃ |
| Ia.328 | —CH₂—CH(CN)—CO—OC₂H₅ |
| Ia.329 | —CH₂—CH(CN)—CO—O(n-C₃H₇) |
| Ia.330 | —CH₂—CH(CN)—CO—O(n-C₄H₉) |
| Ia.331 | —CH₂—CH(CN)—CO—OCH(CH₃)₂ |
| Ia.332 | —CH₂—CH(CN)—CO—OCH₂—CH(CH₃)₂ |
| Ia.333 | —CH₂—CH(CN)—CO—OCH(CH₃)—C₂H₅ |
| Ia.334 | —CH₂—CH(CN)—CO—OC(CH₃)₃ |
| Ia.335 | —CH₂—CH(CN)—CO—OCH₂—CH=CH₂ |
| Ia.336 | —CH₂—CH(CN)—CO—OCH₂—C≡CH |
| Ia.337 | —CH₂—CH(CN)—CO—OCH₂—CO—OCH₃ |
| Ia.338 | —CH₂—CH(CN)—CO—OCH₂—CO—OC₂H₅ |
| Ia.339 | —CH₂—CH(CN)—CO—OCH₂—CO—N(CH₃)₂ |
| Ia.340 | —CH₂—CH(CN)—CO—OCH(CH₃)—CO—OCH₃ |
| Ia.341 | —CH₂—CH(CN)—CO—OCH(CH₃)—CO—OC₂H₅ |
| Ia.342 | —CH₂—CH(CN)—CO—OCH(CH₃)—CO—N(CH₃)₂ |
| Ia.343 | —CH=C(Cl)—CO—OH |
| Ia.344 | —CH=C(Cl)—CO—OCH₃ |
| Ia.345 | —CH=C(Cl)—CO—OC₂H₅ |
| Ia.346 | —CH=C(Cl)—CO—O(n-C₃H₇) |
| Ia.347 | —CH=C(Cl)—CO—O(n-C₄H₉) |
| Ia.348 | —CH=C(Cl)—CO—OCH(CH₃)₂ |
| Ia.349 | —CH=C(Cl)—CO—OCH₂—CH(CH₃)₂ |
| Ia.350 | —CH=C(Cl)—CO—OCH(CH₃)—C₂H₅ |
| Ia.351 | —CH=C(Cl)—CO—OC(CH₃)₃ |
| Ia.352 | —CH=C(Cl)—CO—OCH₂—CH=CH₂ |
| Ia.353 | —CH=C(Cl)—CO—OCH₂—C≡CH |
| Ia.354 | —CH=C(Cl)—CO—OCH₂—CO—OCH₃ |
| Ia.355 | —CH=C(Cl)—CO—OCH₂—CO—OC₂H₅ |
| Ia.356 | —CH=C(Cl)—CO—OCH₂—CO—N(CH₃)₂ |
| Ia.357 | —CH=C(Cl)—CO—OCH(CH₃)—CO—OCH₃ |
| Ia.358 | —CH=C(Cl)—CO—OCH(CH₃)—CO—OC₂H₅ |
| Ia.359 | —CH=C(Cl)—CO—OCH(CH₃)—CO—N(CH₃)₂ |
| Ia.360 | —CH=C(Br)—CO—OH |
| Ia.361 | —CH=C(Br)—CO—OCH₃ |
| Ia.362 | —CH=C(Br)—CO—OC₂H₅ |
| Ia.363 | —CH=C(Br)—CO—O(n-C₃H₇) |
| Ia.364 | —CH=C(Br)—CO—O(n-C₄H₉) |
| Ia.365 | —CH=C(Br)—CO—OCH(CH₃)₂ |
| Ia.366 | —CH=C(Br)—CO—OCH₂—CH(CH₃)₂ |
| Ia.367 | —CH=C(Br)—CO—OCH(CH₃)—C₂H₅ |
| Ia.368 | —CH=C(Br)—CO—OC(CH₃)₃ |
| Ia.369 | —CH=C(Br)—CO—OCH₂—CH=CH₂ |
| Ia.370 | —CH=C(Br)—CO—OCH₂—C≡CH |
| Ia.371 | —CH=C(Br)—CO—OCH₂—CO—OCH₃ |
| Ia.372 | —CH=C(Br)—CO—OCH₂—CO—OC₂H₅ |
| Ia.373 | —CH=C(Br)—CO—OCH₂—CO—N(CH₃)₂ |
| Ia.374 | —CH=C(Br)—CO—OCH(CH₃)—CO—OCH₃ |
| Ia.375 | —CH=C(Br)—CO—OCH(CH₃)—CO—OC₂H₅ |
| Ia.376 | —CH=C(Br)—CO—OCH(CH₃)—CO—N(CH₃)₂ |
| Ia.377 | —CH=C(CN)—CO—OH |
| Ia.378 | —CH=C(CN)—CO—OCH₃ |
| Ia.379 | —CH=C(CN)—CO—OC₂H₅ |
| Ia.380 | —CH=C(CN)—CO—O(n-C₃H₇) |
| Ia.381 | —CH=C(CN)—CO—O(n-C₄H₉) |
| Ia.382 | —CH=C(CN)—CO—OCH(CH₃)₂ |
| Ia.383 | —CH=C(CN)—CO—OCH₂—CH(CH₃)₂ |
| Ia.384 | —CH=C(CN)—CO—OCH(CH₃)—C₂H₅ |
| Ia.385 | —CH=C(CN)—CO—OC(CH₃)₃ |
| Ia.386 | —CH=C(CN)—CO—OCH₂—CH=CH₂ |
| Ia.387 | —CH=C(CN)—CO—OCH₂—C≡CH |
| Ia.388 | —CH=C(CN)—CO—OCH₂—CO—OCH₃ |
| Ia.389 | —CH=C(CN)—CO—OCH₂—CO—OC₂H₅ |
| Ia.390 | —CH=C(CN)—CO—OCH₂—CO—N(CH₃)₂ |
| Ia.391 | —CH=C(CN)—CO—OCH(CH₃)—CO—OCH₃ |
| Ia.392 | —CH=C(CN)—CO—OCH(CH₃)—CO—OC₂H₅ |
| Ia.393 | —CH=C(CN)—CO—OCH(CH₃)—CO—N(CH₃)₂ |
| Ia.394 | —CO—SCH₃ |
| Ia.395 | —CO—SC₂H₅ |
| Ia.396 | —CO—S(n-C₃H₇) |
| Ia.397 | —CO—S(n-C₄H₉) |
| Ia.398 | —CO—SCH(CH₃)₂ |
| Ia.399 | —CO—SCH₂—CH(CH₃)₂ |
| Ia.400 | —CO—SCH(CH₃)—C₂H₅ |
| Ia.401 | —CO—SC(CH₃)₃ |
| Ia.402 | —CO—SCH₂—CH=CH₂ |
| Ia.403 | —CO—SCH₂—C≡CH |
| Ia.404 | —CO—SCH₂—CO—OCH₃ |
| Ia.405 | —CO—SCH₂—CO—OC₂H₅ |
| Ia.406 | —CO—NH₂ |
| Ia.407 | —CO—NH—CH₃ |
| Ia.408 | —CO—N(CH₃)₂ |
| Ia.409 | —CO—NH—C₂H₅ |
| Ia.410 | —CO—N(C₂H₅)₂ |
| Ia.411 | —CO—NH-(n-C₃H₇) |
| Ia.412 | —CO—N(n-C₃H₇)₂ |
| Ia.413 | —CO—NH-(n-C₄H₉) |
| Ia.414 | —CO—N(n-C₄H₉)₂ |
| Ia.415 | —CO—NH—CH(CH₃)₂ |
| Ia.416 | —CO—N[CH(CH₃)₂]₂ |
| Ia.417 | —CO—NH—CH₂—CH(CH₃)₂ |
| Ia.418 | —CO—NH[CH₂—CH(CH₃)₂]₂ |
| Ia.419 | —CO—NH—CH₂—CH=CH₂ |
| Ia.420 | —CO—N(CH₂—CH=CH₂)₂ |

TABLE 1-continued

Ia

[Structure: 3-(4-chloro-3-(XR⁶)phenyl)-5-methyl-1-(methylsulfonyl)-1H-pyrazole]

| No. | —XR⁶ |
|---|---|
| Ia.421 | —CO—NH—CH₂C≡CH |
| Ia.422 | —CO—N(CH₂—C≡CH)₂ |
| Ia.423 | —CO—NH—CH₂—CO—OCH₃ |
| Ia.424 | —CO—N(CH₃)—CH₂—CO—OCH₃ |
| Ia.425 | —CO—NH—CH₂—CO—OC₂H₅ |
| Ia.426 | —CO—N(CH₃)—CH₂—CO—OC₂H₅ |
| Ia.427 | —CO—NH—CH₂—CO—N(CH₃)₂ |
| Ia.428 | —CO—N(CH₃)—CH₂—CO—N(CH₃)₂ |
| Ia.429 | —CO—NH—CH(CH₃)—CO—OCH₃ |
| Ia.430 | —CO—N(CH₃)—CH(CH₃)—CO—OCH₃ |
| Ia.431 | —CO—NH—CH(CH₃)—CO—OC₂H₅ |
| Ia.432 | —CO—N(CH₃)—CH(CH₃)—CO—OC₂H₅ |
| Ia.433 | —CO—NH—CH(CH₃)—CO—N(CH₃)₂ |
| Ia.434 | —CO—N(CH₃)—CH(CH₃)—CO—N(CH₃)₂ |
| Ia.435 | —CO-(pyrrolidin-1-yl) |
| Ia.436 | —CO-(piperidin-1-yl) |
| Ia.437 | —CO-(2-methoxycarbonylpyrrolidin-1-yl) |
| Ia.438 | —CO-(2-methoxycarbonylpiperidin-1-yl) |
| Ia.439 | —CH₂—CH(Cl)—CO—NH₂ |
| Ia.440 | —CH₂—CH(Cl)—CO—NH—CH₃ |
| Ia.441 | —CH₂—CH(Cl)—CO—N(CH₃)₂ |
| Ia.442 | —CH₂—CH(Cl)—CO—NH—C₂H₅ |
| Ia.443 | —CH₂—CH(Cl)—CO—N(C₂H₅)₂ |
| Ia.444 | —CH₂—CH(Cl)—CO—NH-(n-C₃H₇) |
| Ia.445 | —CH₂—CH(Cl)—CO—N(n-C₃H₇)₂ |
| Ia.446 | —CH₂—CH(Cl)—CO—NH-(n-C₄H₉) |
| Ia.447 | —CH₂—CH(Cl)—CO—N(n-C₄H₉)₂ |
| Ia.448 | —CH₂—CH(Cl)—CO—NH—CH₂—CO—OCH₃ |
| Ia.449 | —CH₂—CH(Cl)—CO—N(CH₃)—CH₂—CO—OCH₃ |
| Ia.450 | —CH₂—CH(Cl)—CO—NH—CH₂—CO—OC₂H₅ |
| Ia.451 | —CH₂—CH(Cl)—CO—N(CH₃)—CH₂—CO—OC₂H₅ |
| Ia.452 | —CH₂—CH(Cl)—CO—NH—CH₂—CO—N(CH₃)₂ |
| Ia.453 | —CH₂—CH(Cl)—CO—N(CH₃)—CH₂—CO—N(CH₃)₂ |
| Ia.454 | —CH₂—CH(Cl)—CO—NH—CH(CH₃)—CO—OCH₃ |
| Ia.455 | —CH₂—CH(Cl)—CO—N(CH₃)—CH(CH₃)—CO—OCH₃ |
| Ia.456 | —CH₂—CH(Cl)—CO—NH—CH(CH₃)—CO—OC₂H₅ |
| Ia.457 | —CH₂—CH(Cl)—CO—N(CH₃)—CH(CH₃)—CO—OC₂H₅ |
| Ia.458 | —CH₂—CH(Cl)—CO-(pyrrolidin-1-yl) |
| Ia.459 | —CH₂—CH(Cl)—CO-(piperidin-1-yl) |
| Ia.460 | —CH₂—CH(Cl)—CO-(2-methoxycarbonylpyrrolidin-1-yl) |
| Ia.461 | —CH₂—CH(Cl)—CO-(2-methoxycarbonylpiperidin-1-yl) |
| Ia.462 | —CH₂—CH(Br)—CO—NH₂ |
| Ia.463 | —CH₂—CH(Br)—CO—NH—CH₃ |
| Ia.464 | —CH₂—CH(Br)—CO—N(CH₃)₂ |
| Ia.465 | —CH₂—CH(Br)—CO—NH—C₂H₅ |
| Ia.466 | —CH₂—CH(Br)—CO—N(C₂H₅)₂ |
| Ia.467 | —CH₂—CH(Br)—CO—NH-(n-C₃H₇) |
| Ia.468 | —CH₂—CH(Br)—CO—N(n-C₃H₇)₂ |
| Ia.469 | —CH₂—CH(Br)—CO—NH-(n-C₄H₉) |
| Ia.470 | —CH₂—CH(Br)—CO—N(n-C₄H₉)₂ |
| Ia.471 | —CH₂—CH(Br)—CO—NH—CH₂—CO—OCH₃ |
| Ia.472 | —CH₂—CH(Br)—CO—N(CH₃)—CH₂—CO—OCH₃ |
| Ia.473 | —CH₂—CH(Br)—CO—NH—CH₂—CO—OC₂H₅ |
| Ia.474 | —CH₂—CH(Br)—CO—N(CH₃)—CH₂—CO—OC₂H₅ |
| Ia.475 | —CH₂—CH(Br)—CO—NH—CH₂—CO—N(CH₃)₂ |
| Ia.476 | —CH₂—CH(Br)—CO—N(CH₃)—CH₂—CO—N(CH₃)₂ |
| Ia.477 | —CH₂—CH(Br)—CO—NH—CH(CH₃)—CO—OCH₃ |
| Ia.478 | —CH₂—CH(Br)—CO—N(CH₃)—CH(CH₃)—CO—OCH₃ |
| Ia.479 | —CH₂—CH(Br)—CO—NH—CH(CH₃)—CO—OC₂H₅ |
| Ia.480 | —CH₂—CH(Br)—CO—N(CH₃)—CH(CH₃)—CO—OC₂H₅ |
| Ia.481 | —CH₂—CH(Br)—CO-(pyrrolidin-1-yl) |
| Ia.482 | —CH₂—CH(Br)—CO-(piperidin-1-yl) |
| Ia.483 | —CH₂—CH(Br)—CO-(2-methoxycarbonylpyrrolidin-1-yl) |
| Ia.484 | —CH₂—CH(Br)—CO-(2-methoxycarbonylpiperidin-1-yl) |
| Ia.485 | —CH₂—CH(CN)—CO—NH₂ |
| Ia.486 | —CH₂—CH(CN)—CO—NH—CH₃ |
| Ia.487 | —CH₂—CH(CN)—CO—N(CH₃)₂ |
| Ia.488 | —CH₂—CH(CN)—CO—NH—C₂H₅ |
| Ia.489 | —CH₂—CH(CN)—CO—N(C₂H₅)₂ |
| Ia.490 | —CH₂—CH(CN)—CO—NH-(n-C₃H₇) |
| Ia.491 | —CH₂—CH(CN)—CO—N(n-C₃H₇)₂ |
| Ia.492 | —CH₂—CH(CN)—CO—NH-(n-C₄H₉) |
| Ia.493 | —CH₂—CH(CN)—CO—N(n-C₄H₉)₂ |
| Ia.494 | —CH₂—CH(CN)—CO—NH—CH₂—CO—OCH₃ |
| Ia.495 | —CH₂—CH(CN)—CO—N(CH₃)—CH₂—CO—OCH₃ |
| Ia.496 | —CH₂—CH(CN)—CO—NH—CH₂—CO—OC₂H₅ |
| Ia.497 | —CH₂—CH(CN)—CO—N(CH₃)—CH₂—CO—OC₂H₅ |
| Ia.498 | —CH₂—CH(CN)—CO—NH—CH₂—CO—N(CH₃)₂ |
| Ia.499 | —CH₂—CH(CN)—CO—N(CH₃)—CH₂—CO—N(CH₃)₂ |
| Ia.500 | —CH₂—CH(CN)—CO—NH—CH(CH₃)—CO—OCH₃ |
| Ia.501 | —CH₂—CH(CN)—CO—N(CH₃)—CH(CH₃)—CO—OCH₃ |
| Ia.502 | —CH₂—CH(CN)—CO—NH—CH(CH₃)—CO—OC₂H₅ |
| Ia.503 | —CH₂—CH(CN)—CO—N(CH₃)—CH(CH₃)—CO—OC₂H₅ |
| Ia.504 | —CH₂—CH(CN)—CO-(pyrrolidin-1-yl) |
| Ia.505 | —CH₂—CH(CN)—CO-(piperidin-1-yl) |
| Ia.506 | —CH₂—CH(CN)—CO-(2-methoxycarbonylpyrrolidin-1-yl) |
| Ia.507 | —CH₂—CH(CN)—CO-(2-methoxycarbonylpiperidin-1-yl) |
| Ia.508 | —CH=C(Cl)—CO—NH₂ |
| Ia.509 | —CH=C(Cl)—CO—NH—CH₃ |
| Ia.510 | —CH=C(Cl)—CO—N(CH₃)₂ |
| Ia.511 | —CH=C(Cl)—CO—NH—C₂H₅ |
| Ia.512 | —CH=C(Cl)—CO—N(C₂H₅)₂ |
| Ia.513 | —CH=C(Cl)—CO—NH-(n-C₃H₇) |
| Ia.514 | —CH=C(Cl)—CO—N(n-C₃H₇)₂ |
| Ia.515 | —CH=C(Cl)—CO—NH-(n-C₄H₉) |
| Ia.516 | —CH=C(Cl)—CO—N(n-C₄H₉)₂ |
| Ia.517 | —CH=C(Cl)—CO—NH—CH₂—CO—OCH₃ |
| Ia.518 | —CH=C(Cl)—CO—N(CH₃)—CH₂—CO—OCH₃ |
| Ia.519 | —CH=C(Cl)—CO—NH—CH₂—CO—OC₂H₅ |
| Ia.520 | —CH=C(Cl)—CO—N(CH₃)—CH₂—CO—OC₂H₅ |
| Ia.521 | —CH=C(Cl)—CO—NH—CH₂—CO—N(CH₃)₂ |
| Ia.522 | —CH=C(Cl)—CO—N(CH₃)—CH₂—CO—N(CH₃)₂ |
| Ia.523 | —CH=C(Cl)—CO—NH—CH(CH₃)—CO—OCH₃ |
| Ia.524 | —CH=C(Cl)—CO—N(CH₃)—CH(CH₃)—CO—OCH₃ |
| Ia.525 | —CH=C(Cl)—CO—NH—CH(CH₃)—CO—OC₂H₅ |
| Ia.526 | —CH=C(Cl)—CO—N(CH₃)—CH(CH₃)—CO—OC₂H₅ |
| Ia.527 | —CH=C(Cl)—CO-(pyrrolidin-1-yl) |
| Ia.528 | —CH=C(Cl)—CO-(piperidin-1-yl) |
| Ia.529 | —CH=C(Cl)—CO-(2-methoxycarbonylpyrrolidin-1-yl) |
| Ia.530 | —CH=C(Cl)—CO-(2-methoxycarbonylpiperidin-1-yl) |
| Ia.531 | —CH=C(Br)—CO—NH₂ |
| Ia.532 | —CH=C(Br)—CO—NH—CH₃ |
| Ia.533 | —CH=C(Br)—CO—NH(CH₃)₂ |
| Ia.534 | —CH=C(Br)—CO—NH—C₂H₅ |
| Ia.535 | —CH=C(Br)—CO—N(C₂H₅)₂ |
| Ia.536 | —CH=C(Br)—CO—NH-(n-C₃H₇) |
| Ia.537 | —CH=C(Br)—CO—N(n-C₃H₇)₂ |
| Ia.538 | —CH=C(Br)—CO—NH-(n-C₄H₉) |
| Ia.539 | —CH=C(Br)—CO—N(n-C₄H₉)₂ |
| Ia.540 | —CH=C(Br)—CO—NH—CH₂—CO—OCH₃ |
| Ia.541 | —CH=C(Br)—CO—N(CH₃)—CH₂—CO—OCH₃ |
| Ia.542 | —CH=C(Br)—CO—NH—CH₂—CO—OC₂H₅ |
| Ia.543 | —CH=C(Br)—CO—N(CH₃)—CH₂—CO—OC₂H₅ |
| Ia.544 | —CH=C(Br)—CO—NH—CH₂—CO—N(CH₃)₂ |
| Ia.545 | —CH=C(Br)—CO—N(CH₃)—CH₂—CO—N(CH₃)₂ |
| Ia.546 | —CH=C(Br)—CO—NH—CH(CH₃)—CO—OCH₃ |

TABLE 1-continued

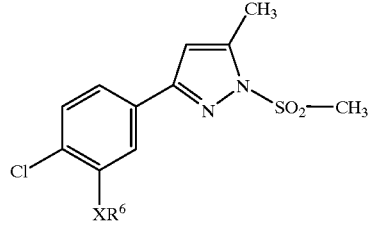

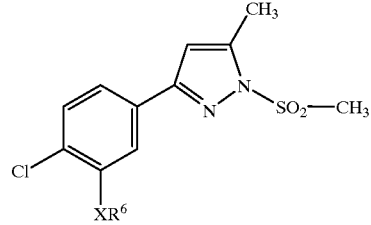

| No. | —XR⁶ |
|---|---|
| Ia.547 | —CH=C(Br)—CO—N(CH₃)—CH(CH₃)—CO—OCH₃ |
| Ia.548 | —CH=C(Br)—CO—NH—CH(CH₃)—CO—OC₂H₅ |
| Ia.549 | —CH=C(Br)—CO—N(CH₃)—CH(CH₃)—CO—OC₂H₅ |
| Ia.550 | —CH=C(Br)—CO-(pyrrolidin-1-yl) |
| Ia.551 | —CH=C(Br)—CO-(piperidin-1-yl) |
| Ia.552 | —CH=C(Br)—CO-(2-methoxycarbonylpyrrolidin-1-yl) |
| Ia.553 | —CH=C(Br)—CO-(2-methoxycarbonylpiperidin-1-yl) |
| Ia.554 | —CH=C(CN)—CO—NH₂ |
| Ia.555 | —CH=C(CN)—CO—NH—CH₃ |
| Ia.556 | —CH=C(CN)—CO—N(CH₃)₂ |
| Ia.557 | —CH=C(CN)—CO—NH—C₂H₅ |
| Ia.558 | —CH=C(CN)—CO—N(C₂H₅)₂ |
| Ia.559 | —CH=C(CN)—CO—NH-(n-C₃H₇) |
| Ia.560 | —CH=C(CN)—CO—N(n-C₃H₇)₂ |
| Ia.561 | —CH=C(CN)—CO—NH-(n-C₄H₉) |
| Ia.562 | —CH=C(CN)—CO—N(n-C₄H₉)₂ |
| Ia.563 | —CH=C(CN)—CO—NH—CH₂—CO—OCH₃ |
| Ia.564 | —CH=C(CN)—CO—N(CH₃)—CH₂—CO—OCH₃ |
| Ia.565 | —CH=C(CN)—CO—NH—CH₂—CO—OC₂H₅ |
| Ia.566 | —CH=C(CN)—CO—N(CH₃)—CH₂—CO—OC₂H₅ |
| Ia.567 | —CH=C(CN)—CO—NH—CH₂—CO—N(CH₃)₂ |
| Ia.568 | —CH=C(CN)—CO—N(CH₃)—CH₂—CO—N(CH₃)₂ |
| Ia.569 | —CH=C(CN)—CO—NH—CH(CH₃)—CO—OCH₃ |
| Ia.570 | —CH=C(CN)—CO—N(CH₃)—CH(CH₃)—CO—OCH₃ |
| Ia.571 | —CH=C(CN)—CO—NH—CH(CH₃)—CO—OC₂H₅ |
| Ia.572 | —CH=C(CN)—CO—N(CH₃)—CH(CH₃)—CO—OC₂H₅ |
| Ia.573 | —CH=C(CN)—CO-(pyrrolidin-1-yl) |
| Ia.574 | —CH=C(CN)—CO-(piperidin-1-yl) |
| Ia.575 | —CH=C(CN)—CO-(2-methoxycarbonylpyrrolidin-1-yl) |
| Ia.576 | —CH=C(CN)—CO-(2-methoxycarbonylpiperidin-1-yl) |
| Ia.577 | —CO—NH—OH |
| Ia.578 | —CO—NH—OCH₃ |
| Ia.579 | —CO—NH—OC₂H₅ |
| Ia.580 | —CO—N(CH₃)—OCH₃ |
| Ia.581 | —CO—N(C₂H₅)—OC₂H₅ |
| Ia.582 | —CH₂—CH(Cl)—CO—NH—OH |
| Ia.583 | —CH₂—CH(Cl)—CO—NH—OCH₃ |
| Ia.584 | —CH₂—CH(Cl)—CO—N(CH₃)—OCH₃ |
| Ia.585 | —CH₂—CH(Cl)—CO—NH—OC₂H₅ |
| Ia.586 | —CH₂—CH(Cl)—CO—N(C₂H₅)—OC₂H₅ |
| Ia.587 | —CH₂—CH(Br)—CO—NH—OH |
| Ia.588 | —CH₂—CH(Br)—CO—NH—OCH₃ |
| Ia.589 | —CH₂—CH(Br)—CO—N(CH₃)—OCH₃ |
| Ia.590 | —CH₂—CH(Br)—CO—NH—OC₂H₅ |
| Ia.591 | —CH₂—CH(Br)—CO—N(C₂H₅)—OC₂H₅ |
| Ia.592 | —CH₂—CH(CN)—CO—NH—OH |
| Ia.593 | —CH₂—CH(CN)—CO—NH—OCH₃ |
| Ia.594 | —CH₂—CH(CN)—CO—N(CH₃)—OCH₃ |
| Ia.595 | —CH₂—CH(CN)—CO—NH—OC₂H₅ |
| Ia.596 | —CH₂—CH(CN)—CO—N(C₂H₅)—OC₂H₅ |
| Ia.597 | —CH=C(Cl)—CO—NH—OH |
| Ia.598 | —CH=C(Cl)—CO—NH—OCH₃ |
| Ia.599 | —CH=C(Cl)—CO—N(CH₃)—OCH₃ |
| Ia.600 | —CH=C(Cl)—CO—NH—OC₂H₅ |
| Ia.601 | —CH=C(Cl)—CO—N(C₂H₅)—OC₂H₅ |
| Ia.602 | —CH=C(Br)—CO—NH—OH |
| Ia.603 | —CH=C(Br)—CO—NH—OCH₃ |
| Ia.604 | —CH=C(Br)—CO—N(CH₃)—OCH₃ |
| Ia.605 | —CH=C(Br)—CO—NH—OC₂H₅ |
| Ia.606 | —CH=C(Br)—CO—N(C₂H₅)—OC₂H₅ |
| Ia.607 | —CH=C(CN)—CO—NH—OH |
| Ia.608 | —CH=C(CN)—CO—NH—OCH₃ |
| Ia.609 | —CH=C(CN)—CO—N(CH₃)—OCH₃ |
| Ia.610 | —CH=C(CN)—CO—NH—OC₂H₅ |
| Ia.611 | —CH=C(CN)—CO—N(C₂H₅)—OC₂H₅ |
| Ia.612 | —O(n-C₅H₁₁) |
| Ia.613 | —O(n-C₆H₁₃) |
| Ia.614 | —OCH₂—CH=CH—Cl |
| Ia.615 | —OCH₂—C≡C—CH₃ |
| Ia.616 | —OCH₂—OC₂H₅ |
| Ia.617 | —OCH₂—CH₂—OC₂H₅ |
| Ia.618 | —OCH₂—CO—O(n-C₃H₇) |
| Ia.619 | —OCH₂—CO—OCH(CH₃)₂ |
| Ia.620 | —OCH₂—CO—O(n-C₄H₉) |
| Ia.621 | —OCH₂—CO—OCH₂—CH(CH₃)₂ |
| Ia.622 | —OCH₂—CO—OCH(CH₃)—C₂H₅ |
| Ia.623 | —OCH₂—CO—O(n-C₅H₁₁) |
| Ia.624 | —OCH₂—CO—O(n-C₆H₁₃) |
| Ia.625 | —OCH₂—CO—NH₂ |
| Ia.626 | —OCH₂—CO—NH—CH₃ |
| Ia.627 | —OCH(CH₃)—CO—O(n-C₃H₇) |
| Ia.628 | —OCH(CH₃)—CO—OCH(CH₃)₂ |
| Ia.629 | —OCH(CH₃)—CO—O(n-C₄H₉) |
| Ia.630 | —OCH(CH₃)—CO—OCH₂—CH(CH₃)₂ |
| Ia.631 | —OCH(CH₃)—CO—OCH(CH₃)—C₂H₅ |
| Ia.632 | —OCH(CH₃)—CO—O(n-C₅H₁₁) |
| Ia.633 | —OCH(CH₃)—CO—O(n-C₆H₁₃) |
| Ia.634 | —OCH(CH₃)—CO—NH₂ |
| Ia.635 | —OCH(CH₃)—CO—NH—CH₃ |
| Ia.636 | —S(n-C₅H₁₁) |
| Ia.637 | —S(n-C₆H₁₃) |
| Ia.638 | —SCH₂—CH=CH—Cl |
| Ia.639 | —SCH₂—C≡C—CH₃ |
| Ia.640 | —SCH₂—OC₂H₅ |
| Ia.641 | —SCH₂—CH₂—OC₂H₅ |
| Ia.642 | —SCH₂—CO—O(n-C₃H₇) |
| Ia.643 | —SCH₂—CO—OCH(CH₃)₂ |
| Ia.644 | —SCH₂—CO—O(n-C₄H₉) |
| Ia.645 | —SCH₂—CO—OCH₂—CH(CH₃)₂ |
| Ia.646 | —SCH₂—CO—OCH(CH₃)—C₂H₅ |
| Ia.647 | —SCH₂—CO—O(n-C₅H₁₁) |
| Ia.648 | —SCH₂—CO—O(n-C₆H₁₃) |
| Ia.649 | —SCH₂—CO—NH₂ |
| Ia.650 | —SCH₂—CO—NH—CH₃ |
| Ia.651 | —SCH(CH₃)—CO—O(n-C₃H₇) |
| Ia.652 | —SCH(CH₃)—CO—OCH(CH₃)₂ |
| Ia.653 | —SCH(CH₃)—CO—O(n-C₄H₉) |
| Ia.654 | —SCH(CH₃)—CO—OCH₂—CH(CH₃)₂ |
| Ia.655 | —SCH(CH₃)—CO—OCH(CH₃)—C₂H₅ |
| Ia.656 | —SCH(CH₃)—CO—O(n-C₅H₁₁) |
| Ia.657 | —SCH(CH₃)—CO—O(n-C₆H₁₃) |
| Ia.658 | —SCH(CH₃)—CO—NH₂ |
| Ia.659 | —SCH(CH₃)—CO—NH—CH₃ |
| Ia.660 | —CH(=NOCH₃)—OCH₃ |
| Ia.661 | —CH(=NOCH₃)—OCH₂—CO—OCH₃ |
| Ia.662 | —CH(=NOCH₃)—OCH₂—CO—OC₂H₅ |
| Ia.663 | —CO—O(n-C₅H₁₁) |
| Ia.664 | —CO—O(n-C₆H₁₃) |
| Ia.665 | —CO—OCH₂—CH=CH—Cl |
| Ia.666 | —CO—OCH₂—C≡C—CH₃ |
| Ia.667 | —CO—OCH₂—CH₂—OC₂H₅ |
| Ia.668 | —CO—OCH₂—CO—O(n-C₃H₇) |
| Ia.669 | —CO—OCH₂—CO—OCH(CH₃)₂ |
| Ia.670 | —CO—OCH₂—CO—O(n-C₄H₉) |
| Ia.671 | —CO—OCH₂—CO—OCH₂—CH(CH₃)₂ |
| Ia.672 | —CO—OCH₂—CO—OCH(CH₃)—C₂H₅ |

TABLE 1-continued

Ia

| No. | —XR⁶ |
|---|---|
| Ia.673 | —CO—OCH₂—CO—O(n-C₅H₁₁) |
| Ia.674 | —CO—OCH₂—CO—O(n-C₆H₁₃) |
| Ia.675 | —CO—OCH₂—CO—NH₂ |
| Ia.676 | —CO—OCH₂—CO—NH—CH₃ |
| Ia.677 | —CO—OCH(CH₃)—CO—O(n-C₃H₇) |
| Ia.678 | —CO—OCH(CH₃)—CO—OCH(CH₃)₂ |
| Ia.679 | —CO—OCH(CH₃)—CO—O(n-C₄H₉) |
| Ia.680 | —CO—OCH(CH₃)—CO—OCH₂—CH(CH₃)₂ |
| Ia.681 | —CO—OCH(CH₃)—CO—OCH(CH₃)—C₂H₅ |
| Ia.682 | —CO—OCH(CH₃)—CO—O(n-C₅H₁₁) |
| Ia.683 | —CO—OCH(CH₃)—CO—O(n-C₆H₁₃) |
| Ia.684 | —CO—OCH(CH₃)—CO—NH₂ |
| Ia.685 | —CO—OCH(CH₃)—CO—NH—CH₃ |
| Ia.686 | —PO(OCH₃)₂ |
| Ia.687 | —PO(OC₂H₅)₂ |
| Ia.688 | —CH₂—PO(OCH₃)₂ |
| Ia.689 | —CH₂—PO(OC₂H₅)₂ |
| Ia.690 | —OCH₂—PO(OCH₃)₂ |
| Ia.691 | —OCH₂—PO(OC₂H₅)₂ |
| Ia.692 | —SCH₂—PO(OCH₃)₂ |
| Ia.693 | —SCH₂—PO(OC₂H₅)₂ |
| Ia.694 | —CO—OCH₂—PO(OCH₃)₂ |
| Ia.695 | —CO—OCH₂—PO(OC₂H₅)₂ |
| Ia.696 | —CH₂—CH(Cl)—PO(OCH₃)₂ |
| Ia.697 | —CH₂—CH(Cl)—PO(OC₂H₅)₂ |
| Ia.698 | —CH₂—CH(Br)—PO(OCH₃)₂ |
| Ia.699 | —CH₂—CH(Br)—PO(OC₂H₅)₂ |
| Ia.700 | —CH=CH—PO(OCH₃)₂ |
| Ia.701 | —CH=CH—PO(OC₂H₅)₂ |
| Ia.702 | —CH=C(Cl)—PO(OCH₃)₂ |
| Ia.703 | —CH=C(Cl)—PO(OC₂H₅)₂ |
| Ia.704 | —CH=C(Br)—PO(OCH₃)₂ |
| Ia.705 | —CH=C(Br)—PO(OC₂H₅)₂ |

Other particularly preferred 1-sulfonyl-3-phenylpyrazoles are those of the formulae Ib to Ii, in particular the compounds Ib.001–Ib.705, which differ from the corresponding compounds Ia.001–Ia.705 only in that $R^3$ is chlorine:

Ib the compounds Ic.001–Ic.705, which differ from the corresponding compounds Ia.001–Ia.705 only in that $R^3$ is bromine:

Ic the compounds Id.001–Id.705, which differ from the corresponding compounds Ia.001–Ia.705 only in that $R^4$ is fluorine:

Id the compounds Ie.001–Ie.705, which differ from the corresponding compounds Ia.001–Ia.705 only in that $R^3$ is chlorine and $R^4$ is fluorine:

Ie the compounds If.001–If.705, which differ from the corresponding compounds Ia.001–Ia.705 only in that $R^3$ is bromine and $R^4$ is fluorine:

If the compounds Ig.001–Ig.705, which differ from the corresponding compounds Ia.001–Ia.705 only in that $R^4$ is chlorine:

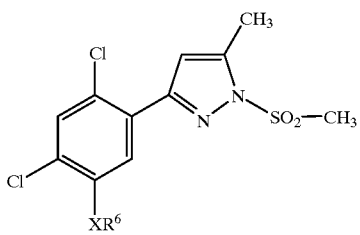

Ig the compounds Ih.001–Ih.705, which differ from the corresponding compounds Ia.001–Ia.705 only in that $R^3$ and $R^4$ are chlorine:

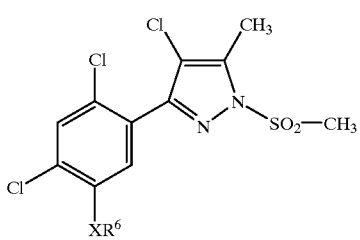

Ih the compounds Ii.001–Ii.705, which differ from the corresponding compounds Ia.001–Ia.705 only in that $R^3$ is bromine and $R^4$ is chlorine:

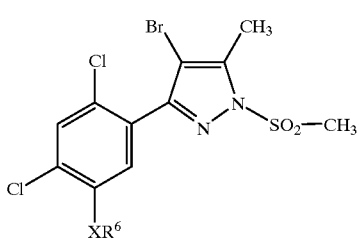

Ii

The 1-sulfonyl-3-phenylpyrazoles of the formula I can be obtained in a variety of ways, in particular following one of the processes below:

A) halogenation of 1-sulfonyl-3-phenylpyrazoles I where $R^3$ is hydrogen:

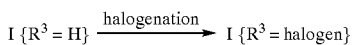

Suitable halogenating agents are, for example, fluorine, DAST (diethylaminosulfur trifluoride), chlorine, N-chlorosuccinimide, sulfuryl chloride, thionyl chloride, phosgene, phosphorus trichloride, phosphorus oxychloride, bromine, N-bromosuccinimide, phosphorus tribromide and phosphorus oxybromide.

The reaction is usually carried out in an inert solvent/diluent, for example in a hydrocarbon such as n-hexane and toluene, a halogenated hydrocarbon, such as carbon tetrachloride and chloroform, an ether, such as methyl tert-butyl ether, an alcohol, such as methanol and ethanol, a carboxylic acid, such as acetic acid, or in an aprotic solvent, such as acetonitrile.

The reaction temperature is usually between the melting and the boiling point of the reaction mixture, preferably from 0 to 100° C.

To obtain as high a yield of the product of value as possible, the halogenating agent is used in about equimolar amounts or in excess up to about five times the molar amount, based on the amount of starting material.

B) Reaction of a phenylpyrazole of the formula II with a sulfonic acid derivative III in the presence of a base:

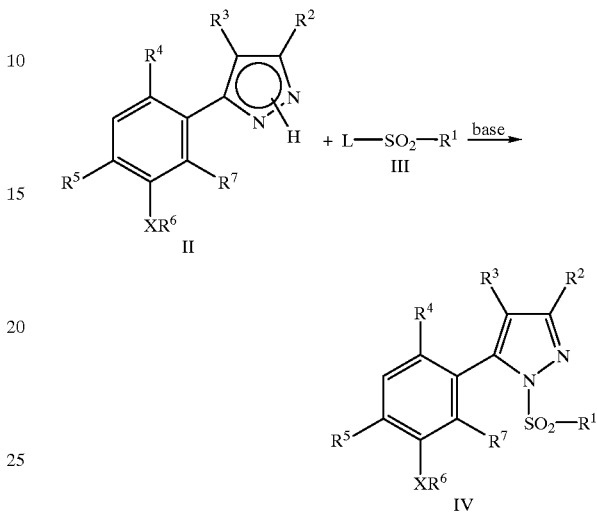

L is a customary leaving group, such as halide or $-O-SO_2-R^1$. The circle in the pyrazole ring of the compound II represents two double bonds.

The sulfonic acid derivative III is preferably a sulfonyl chloride (L=Cl) or the anhydride of the corresponding sulfonic acid (L=O—SO$_2$—R$^1$).

The reaction is usually carried out in an inert solvent/diluent, for example in a hydrocarbon, such as n-hexane and toluene, a halogenated hydrocarbon, such as carbon tetrachloride and chloroform, an ether, such as methyl tert-butyl ether or in a conventional aprotic solvent, such as acetonitrile, dimethylformamide and dimethyl sulfoxide.

Suitable bases are inorganic bases, for example alkali metal carbonates, such as sodium carbonate and potassium carbonate, alkali metal hydroxides, such as sodium hydroxide and potassium hydroxide, alkaline earth metal hydroxides, such as calcium hydroxide, or alkali metal hydrides, such as sodium hydride, and also organic bases, for example tertiary amines, such as triethylamine, Grignard reagents or alkyllithium compounds, such as methylmagnesium chloride and butyllithium.

The reaction temperature is usually between the melting point and the boiling point of the reaction mixture, preferably from 0 to 100° C.

The base and the sulfonic acid derivative III are generally used in about equimolar amounts, based on the amount of II. However, it may be advantageous to use an excess of base and/or III of up to about five times the molar amount, based on the amount of II, to obtain a higher yield of the product of value.

In addition to the products of value I, their regioisomers IV may be formed as byproducts; the latter may be separated off in a conventional manner.

The phenylpyrazoles II are obtainable for example by reaction of diketones V with hydrazine, hydrazine hydrate (i.e. for example an aqueous hydrazine solution), or with a hydrazine salt, such as hydrazine sulfate, in a manner known per se:

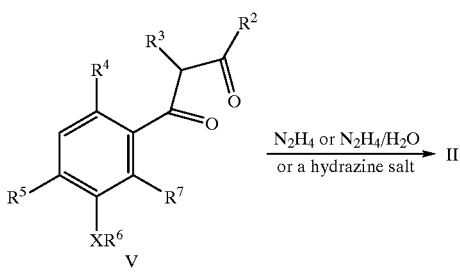

The reaction is usually carried out in water or in an inert organic solvent/diluent, for example a hydrocarbon, such as n-hexane and toluene, a halogenated hydrocarbon, such as carbon tetrachloride and chloroform, an ether, such as methyl tert-butyl ether, an alcohol, such as methanol and ethanol, a carboxylic acid, such as acetic acid, or an aprotic solvent, such as acetonitrile.

The reaction temperature is usually between the melting point and the boiling point of the reaction mixture, preferably from 0 to 100° C.

In general, about equimolar amounts of hydrazine and diketone V are used. However, to optimize the yield of II, it may be advantageous to use an excess of hydrazine of up to about five times the molar amount, based on the amount of V.

Phenylpyrazoles of the formula II in which $R^3$ is halogen are also obtainable for example by halogenating the corresponding compounds II where $R^3$ is hydrogen, as described under A) for the 1-sulfonyl-3-phenylpyrazoles I.

C) Reactions on the phenyl ring

C1) Nitration of 1-sulfonyl-3-phenylpyrazoles I where $XR^6$ is hydrogen and conversion of the products into further compounds of the formula I:

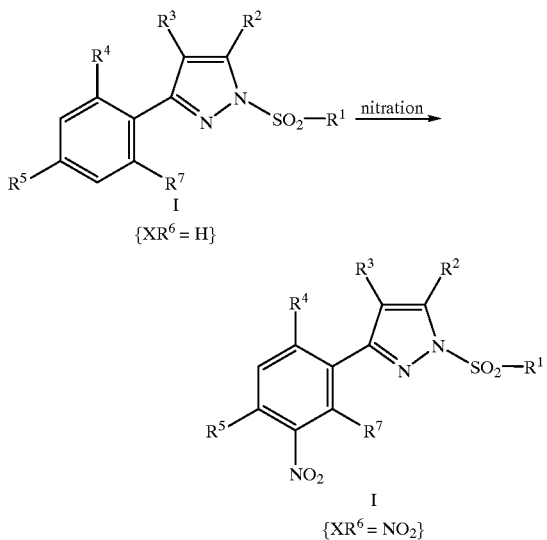

Suitable nitrating agents are, for example, nitric acid in various concentrations, including concentrated and fuming nitric acid, mixtures of sulfuric acid and nitric acid, acetyl nitrates and alkyl nitrates.

The reaction can be carried out either without using a solvent in an excess of the nitrating agent, or in an inert solvent or diluent, suitable solvents or diluents being, for example, water, mineral acids, organic acids, halogenated hydrocarbons such as methylene chloride, anhydrides such as acetic anhydride as well as mixtures of these.

Starting material I $\{XR^6=H\}$ and nitrating agent are advantageously employed in about equimolar amounts; however, to optimize the conversion of the starting material it may be advantageous to use an excess of nitrating agent, up to about 10 times the molar amount.

When the reaction is carried out without a solvent in the nitrating agent the latter is present in an even greater excess.

The reaction temperature is usually from (−100) to 200° C., preferably from (−30) to 50° C. The products of this step where $XR^6$ $NO_2$ can then be reduced to the compounds I where $XR^6$=amino or —NHOH:

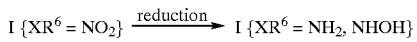

The reduction can be carried out using a metal such as iron, zinc or tin under acid reaction conditions or a complex hydride, such as lithium aluminum hydride and sodium borohydride, suitable solvents being—depending on the reducing agent chosen—for example water, alcohols, such as methanol, ethanol and isopropanol, or ethers, such as diethyl ether, methyl tert-butyl ether, dioxane, tetrahydrofuran and ethylene glycol dimethyl ether.

If the reduction is carried out using a metal, the reaction is preferably carried out without a solvent in an inorganic acid, in particular in concentrated or dilute hydrochloric acid, or in an organic acid such as acetic acid. However, it is also possible to add an inert solvent, for example one of the solvents mentioned above, to the acid.

Advantageously, the starting material I $\{XR^6=NO_2\}$ and the reducing agent are used in about eguimolar amounts; however, to optimize the reaction it may be advantageous to use an excess of one of the two components, up to about 10 times the molar amount.

The amount of acid is not critical. To ensure as complete a reduction of the starting material as possible, it is advantageous to use at least an equivalent amount of acid.

The reaction temperature is usually from (−30) to 200° C., preferably from 0 to 80° C.

For work-up, the reaction mixture is usually diluted with water and the product is isolated by filtration, crystallization or extraction with a substantially water-immiscible solvent, for example ethyl acetate, diethyl ether or methylene chloride. If desired, the product can then be purified in a conventional manner.

The nitro group of the compounds I where $XR^6$=nitro can also be hydrogenated catalytically using hydrogen. Catalysts suitable for this purpose are, for example, Raney nickel, palladium on activated carbon, palladium oxide, platinum and platinum oxide, an amount of catalyst of from 0.05 to 10.0 mol %, based on the compound to be reduced, generally being sufficient.

The reaction is carried out without a solvent or in an inert solvent or diluent, for example in acetic acid, a mixture of acetic acid and water, ethyl acetate, ethanol or toluene.

After the removal of the catalyst, the reaction solution can be worked up in a conventional manner to afford the product.

The hydrogenation can be carried out under atmospheric pressure or under elevated pressure. The amino group can then be diazotized in a conventional manner. The diazonium salts then give access to the compounds I where $XR^6$ cyano or halogen {for the Sandmeyer reaction, cf. for example Houben-weyl, Methoden der Organischen Chemie, Georg Thieme Verlag Stuttgart, Vol. 5/4, 4th Edition, 1960, p. 438ff.}, $XR^6$=hydroxyl {for generating phenols by heating diazonium salts, cf. for example Org. Synth. Coll. Vol. 3 (1955), p. 130}, $XR^6$=mercapto or $C_1$–$C_6$-alkylthio {cf. for example Houben-Weyl, Methoden der Organischen Chemie, Georg Thieme Verlag Stuttgart, Vol. Ell 1984, p. 43 and 176}, $XR^6$=halosulfonyl {cf. for example Houben-Weyl, Methoden der Organischen Chemie, Georg Thieme Verlag Stuttgart, Vol. Ell 1984, p. 1069f.}, $XR^6$=for example —$CH_2$—CH(halogen)—C—O—Y—$R^8$, —CH=C(halogen)—CO—Y—$R^8$ {these are generally products of a Meerwein arylation; cf. for example C. S. Rondestredt, Org. React. 11 (1960), 189 and B. P. Doyle et al., J. Org. Chem. 42 (1977), 2431}:

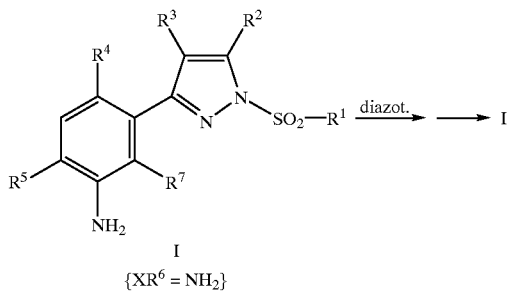

{$XR^6$ = $NH_2$}

I {$XR^6$ = e.g. CN, halogen, OH, SH, —S—Y—$R^8$,
—$SO_2$-halogen, —$CH_2$—CH-(halogen)-CO—O—Y—$R^8$,
—CH=C(halogen)-CO—O—Y—$R^8$,
—$CH_2$—CH(halogen)-PO(O—Y—$R^8$)$_2$,
—CH=C(halogen)-PO(O—Y—$R^8$)$_2$}

The diazonium salt is generally obtained in a manner known per se by reacting I where $XR^6$=amino in an aqueous solution of acid, for example in hydrochloric acid, hydrobromic acid or sulfuric acid with a nitrite such as sodium nitrite and potassium nitrite.

Alternatively, it is possible to carry out the reaction in the absence of water, for example in glacial acetic acid containing hydrogen chloride, in absolute alcohol. in dioxane or tetrahydrofuran, in acetonitrile or in acetone, treating the starting material (I where $XR^6$ $NH_2$) with a nitrite such as tert-butyl nitrite and isopentyl nitrite.

The conversion of the diazonium salt obtained in this manner into the corresponding compound I where $XR^6$ =cyano, chlorine, bromine or iodine is particularly preferably carried out by treatment with a solution or suspension of a copper(I) salt such as copper(I) cyanide, chloride, bromide and iodide, or with a solution of an alkali metal salt.

The conversion of the diazonium salt obtained in this manner into the corresponding compound I where $XR^6$ hydroxyl is advantageously carried out by treatment with an aqueous acid, preferably sulfuric acid. The addition of a copper(II) salt such as copper(II) sulfate can have a positive effect on the course of the reaction.

The reaction is generally carried out at from 0 to 100° C., preferably at the boiling point of the reaction mixture.

Compounds I where $XR^6$=mercapto, $C_1$–$C_6$-alkylthio or halosulfonyl are usually obtained by reacting the diazonium salt with hydrogen sulfide, an alkali metal sulfide, a dialkyl disulfide such as dimethyl disulfide, or with sulfur dioxide.

The Meerwein arylation usually entails reacting the diazonium salts with alkenes or alkynes. The alkene or alkyne is preferably employed in excess of up to about 3000 mol %, based on the amount of the diazonium salt.

The above-described reactions of the diazonium salt can be carried out for example in water, in aqueous hydrochloric acid or hydrobromic acid, in a ketone, such as acetone, diethyl ketone and methyl ethyl ketone, in a nitrile, such as acetonitrile, in an ether, such as dioxane and tetrahydrofuran, or in an alcohol, such as methanol and ethanol.

Unless stated otherwise for the individual reactions, the reaction temperatures are usually from (–30) to 50° C.

All reaction partners are preferably employed in approximately stoichiometric amounts, but an excess of one or the other component of up to about 3000 mol % may be advantageous.

The compounds I where $XR^6$=mercapto can also be obtained by reducing corresponding compounds I where $XR^6$ halosulfonyl:

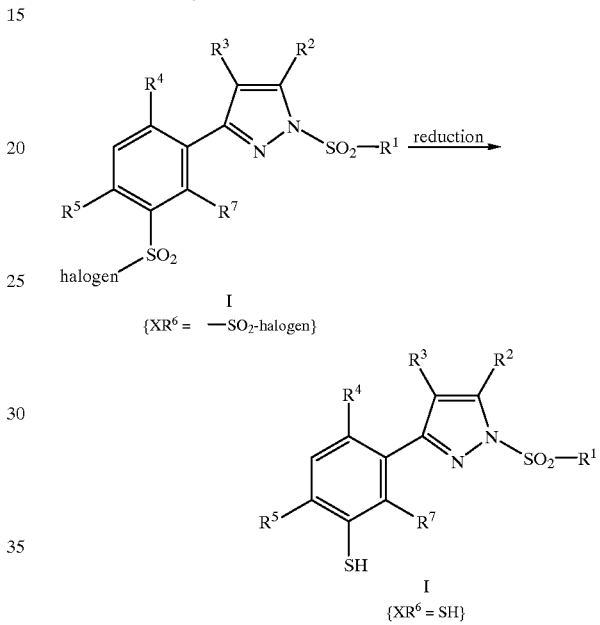

{$XR^6$ = —$SO_2$-halogen}

{$XR^6$ = SH}

Suitable reducing agents are, for example, transition metals such as iron, zinc and tin (cf. for example "The Chemistry of the Thiol Group", John Wiley, 1974, p. 216).

C.2) Halosulfonation of 1-sulfonyl-3-phenylpyrazoles I where $XR^6$ is hydrogen:

I {$XR^6$=H}→I {$XR^6$=—$SO_2$-halogen}

The halosulfonation can be carried out in the absence of a solvent in an excess of sulfonating agent, or in an inert solvent/diluent, for example in a halogenated hydrocarbon, an ether, an alkylnitrile or a mineral acid.

Chlorosulfonic acid is the preferred agent as well as the preferred solvent.

The amount of sulfonating agent used is usually slightly less (up to about 95 mol %) or an excess of 1 to 5 times the molar amount of the starting material I (where $XR^6$=H). In the absence of an inert solvent, it may be advantageous to employ an even larger excess.

The reaction temperature is usually from 0° C. to the boiling point of the reaction mixture.

For work-up, the reaction mixture is mixed for example with water, whereupon the product can be isolated as usual.

C.3) Balogenation of 1-sulfonyl-3-phenylpyrazoles I where $XR^6$ is methyl, and conversion of the products into further compounds of the formula I:

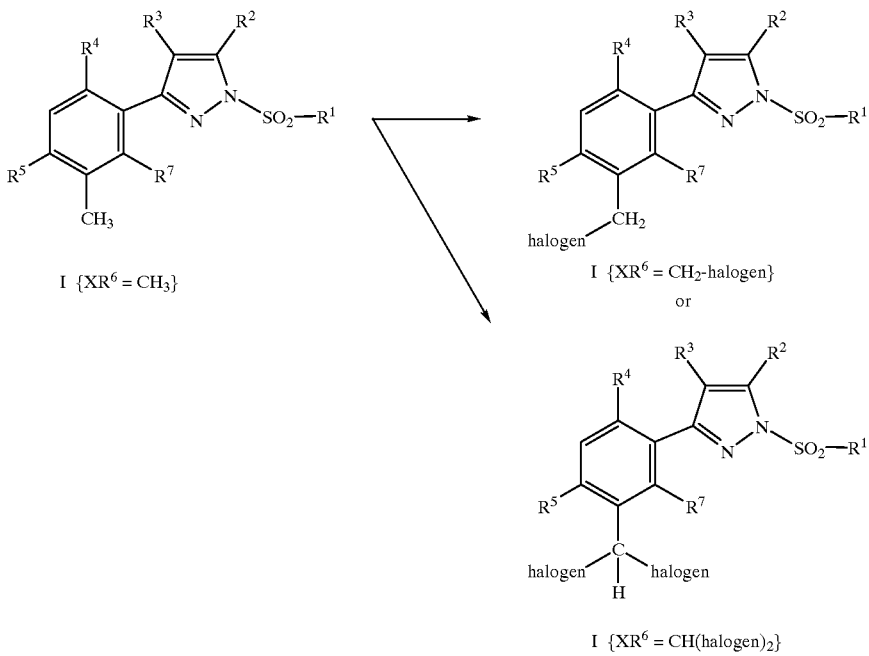

Examples of suitable solvents include organic acids, inorganic acids, aliphatic or aromatic hydrocarbons which may be halogenated, and also ethers, sulfides, sulfoxides and sulfones.

Suitable halogenating agents are, for example, chlorine, bromine, n-bromosuccinimide, n-chlorosuccinimide or sulfuryl chloride. Depending on the starting material and the halogenating agent used, the addition of a free-radical initiator, for example an organic peroxide such as dibenzoyl peroxide or an azo compound such as azobisisobutyronitrile, or irradiation with light, may have an advantageous effect on the course of the reaction.

The amount of halogenating agent is not critical. Both substoichiometric amounts and large excesses of halogenating agent, based on the compound I to be halogenated (where $XR^6$=methyl), are possible. When using a free-radical initiator, a catalytic amount is usually sufficient.

The reaction temperature is usually from (−100) to 200° C., mainly from 10 to 100° C. or the boiling point of the reaction mixture.

By nucleophilic substitution, those halogenation products I where $XR^6$ =—$CH_2$-halogen can be converted into their corresponding ethers, thioethers, esters, amines or a hydroxylamines:

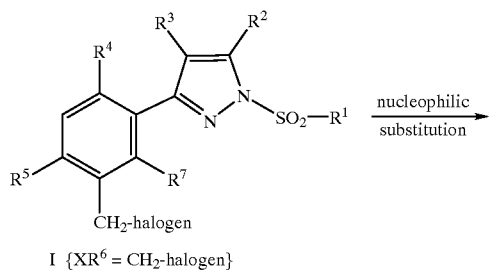

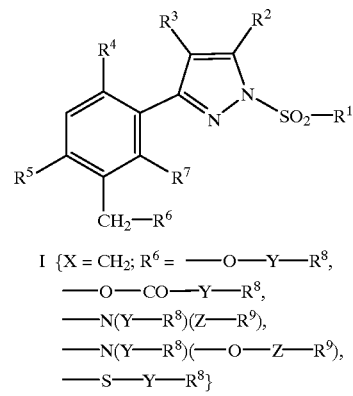

I {X = $CH_2$; $R^6$ = —O—Y—$R^8$,
—O—CO—Y—$R^8$,
—N(Y—$R^8$)(Z—$R^9$),
—N(Y—$R^8$)(—O—Z—$R^9$),
—S—Y—$R^8$}

The nucleophile used is either a suitable alcohol, thiol, carboxylic acid or amine, the reaction in this case being preferably carried out in the presence of a base (for example an alkali metal hydroxide or an alkaline earth metal hydroxide or an alkali metal carbonate or alkaline earth metal carbonate), or the alkali metal salts of these compounds obtained by reaction of the alcohol, thiol, carboxylic acid or amine with a base (for example an alkali metal hydride).

Particularly suitable solvents are aprotic organic solvents, for example tetrahydrofuran, dimethylformamide and dimethylsulfoxide, or hydrocarbons, such as toluene and n-hexane.

The reaction is carried out at a temperature from the melting point to the boiling point of the reaction mixture, preferably at from 0 to 100° C.

Those halogenation products I where $XR^6$=—CH(halogen)$_2$ can be hydrolyzed to the corresponding aldehydes (I where $XR^6$=CHO). The latter can in turn be oxidized to the compounds I where $XR^6$=COOH:

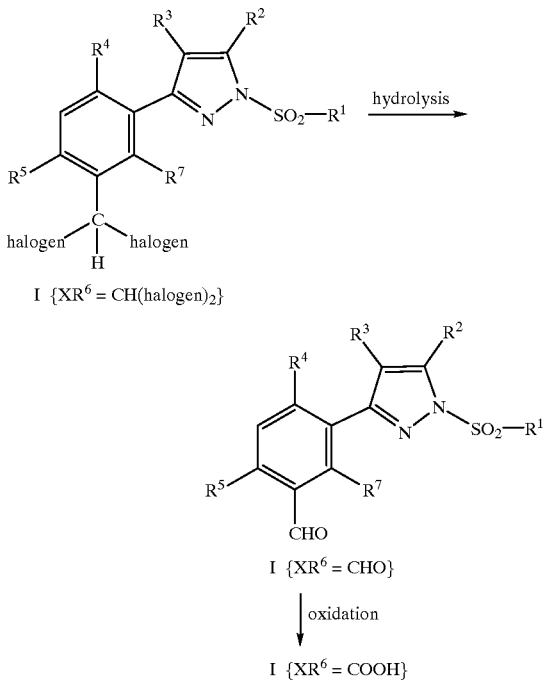

I {XR$^6$ = CH(halogen)$_2$}

↓ hydrolysis

I {XR$^6$ = CHO}

↓ oxidation

I {XR$^6$ = COOH}

The hydrolysis of the compounds I where XR$^6$ =dihalomethyl is preferably carried out under acidic condition, in particular in the absence of a solvent in hydrochloric acid, acetic acid, formic acid or sulfuric acid, or in an aqueous solution of one of the acids mentioned, for example in a mixture of acetic acid and water (for example 3:1).

The reaction temperature is usually at from 0 to 120° C.

The oxidation of the hydrolysis products I where XR$^6$ formyl to the corresponding carboxylic acids can be carried out in a manner known per se, for example according to Kornblum (cf. in particular pages 179 to 181 of the volume "Methods for the Oxidation of Organic Compounds" of A. B. Haines, Academic Press 1988, in the series "Best Synthetic Methods").

A suitable solvent is for example dimethyl sulfoxide.

The compounds I where XR$^6$=formyl can also be converted in a manner known per se into olefins I with X=unsubstituted or substituted ethene-1,2-diyl:

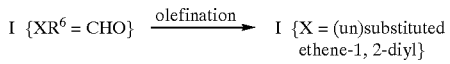

I {XR$^6$ = CHO} —olefination→ I {X = (un)substituted ethene-1, 2-diyl}

The olefination is preferably carried out by the method of Wittig or one of its modifications, suitable reaction partners being phosphorus ylides, phosphonium salts and phosphonates, or by Aldol condensation.

If a phosphonium salt or a phosphonate is used, it is advantageous to carry out the reaction in the presence of a base, particularly suitable bases being alkali metal alkyls, such as n-butyllithium, alkali metal hydrides and alkoxides, such as sodium hydride, sodium ethoxide and potassium tert-butoxide, and alkali metal hydroxides and alkaline earth metal hydroxides, such as calcium hydroxide.

For a complete conversion, all reaction partners are employed in a ratio which is about stoichiometric; however, preference is given to using an excess of the phosphorus compound and/or base of up to about 10 molt, based on the starting material I (where XR$^6$=formyl).

The reaction temperature is generally from (–40) to

The 1-sulfonyl-3-phenylpyrazoles I where XR$^6$=formyl can be converted into the compounds I where XR$^6$=—CO—Y—R$^8$ in a manner known per se, for example by reaction with a suitable organometal compound Me—Y—R$^8$- where Me is preferably lithium or magnesium - and subsequent oxidation of the alcohols obtained in this reaction (cf. for example J. March, Advanced Organic Chemistry, 3rd ed., John wiley, New York 1985, p. 816ff. and 1057ff.).

The compounds I where XR$^6$ —CO—Y—R$^8$ can in turn be reacted further in a wittig reaction.

The phosphonium salts, phosphonates or phosphorus ylides required as reaction partner which are not already known can be prepared in a conventional manner {cf. for example Houben-Weyl, Methoden der Organischen Chemie, Vol. El, p. 636ff. and Vol. E2, p. 345ff., Georg Thieme Verlag Stuttgart 1982; Chem. Ber. S (1962) 3993}.

Further possible ways to prepare other 1-sulfonyl-3-phenylpyrazoles I from compounds I where XR$^6$=formyl include the known Aldol condensation and Knoevenagel or Perkin condensation reactions. Suitable reaction conditions for these methods are described for example in Nielson, Org. React. 16 (1968), 1ff {Aldol condensation} Org. React. 15 (1967), 204ff. {Knoevenagel condensation} and Johnson, Org. React. 1 (1942), 210ff. {Perkin condensation}.

In general, the compounds I where XR$^6$=—CO—Y—R$^8$ can also be converted into their corresponding oximes in a manner known per se {cf. for example Houben-Weyl, Methoden der Organischen Chemie, Georg Thieme Verlag Stuttgart, Vol. 10/4, 4th edition, 1968, p. 55ff. and p. 73ff.}:

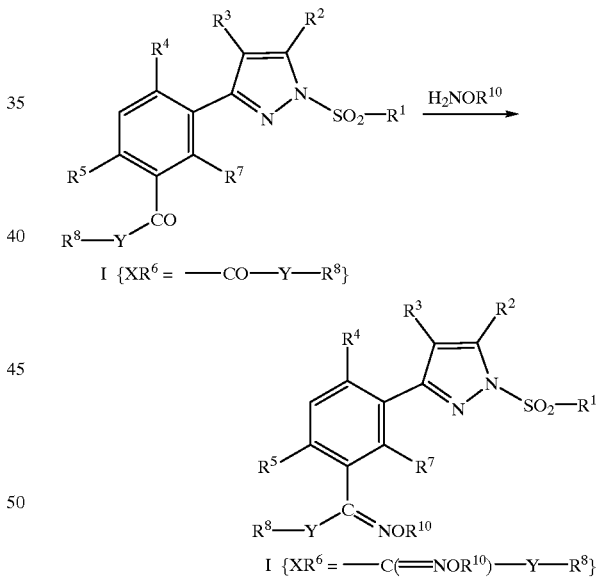

I {XR$^6$ = —CO—Y—R$^8$}

I {XR$^6$ = —C(=NOR$^{10}$)—Y—R$^8$}

C.4) Synthesis of ethers, thioethers, amines, esters, amides, sulfonamides, thioesters, hydroximic esters, hydroxyl-amines, sulfonic acid derivatives, oximes or carboxylic acid derivatives:

1-Sulfonyl-3-phenylpyrazoles I where R$^6$ is hydroxyl, amino, —NH—Y—R$^8$, hydroxylamino, —N(Y—R$^8$)—OH, —NH-O—Y—R$^8$, mercapto, halosulfonyl, —C(=NOH)—Y—R$^8$, carboxyl or —CO—NEH Z—R$^9$ can be converted in a manner known per se by alkylation, acylation, sulfonation, esterification or amidation into the corresponding ethers {I where R$^6$ =—O—Y—R$^8$}, esters {I where R$^6$=—O—CO—Y—R$^8$}, amines {I where R$^6$=—N(Y—R$^8$)(Z—R$^9$)}, amides {I where R$^6$=—N(Y—R$^8$)—

CO—Z—R⁹}, sulfonamides {I where R⁶=—N(Y—R⁸)—SO₂—Z—R⁹ or —N(SO₂—Y—R⁸)(SO₂—Z—R⁹)}, hydroxylamines {I where R⁶ =—N(Y—R⁸)(O—Z—R⁹)}, thioethers {I where R⁶=—S—Y—R⁸}, sulfonic acid derivatives {I where R⁶ =—SO₂—Y—R⁸, —SO₂—O—Y—R⁸ or —SO₂—N(Y—R⁸)(Z—R⁹)}, oximes {I where R⁶ =—C(=NOR¹)—Y—R⁸}, carboxylic acid derivatives {I where R⁶ =—C—O—Y—R⁸, —CO—S—Y—R⁸, —CO—N(Y—R⁸)(Z—R⁹), —CO—N(Y—R⁸)(O—Z—R⁹)} or hydroximic esters {I where R⁶ =—C(=NOR¹⁰)—O—Y—R⁸}.

Such conversions are described, for example, in Houben-Weyl, Methoden der Organischen Chemie, Georg Thieme Verlag Stuttgart (Vol. H16d, p. 1241ff.; Vol. 6/1a, 4th edition, 1980, p. 262ff.; Vol. 8, 4th edition, 1952, p. 471ff., 516ff., 655ff. and p. 686ff.; Vol. 6/3, 4th edition, 1965, p. 10ff.; Vol. 9, 4th edition, 1955, p. 103ff., 227ff., 343ff., 530ff., 659ff., 745ff. and p. 753ff.; Vol. E5, p. 934ff., 941ff. and p. 1148ff.).

Corresponding reactions can also be carried out using the phenylpyrazoles of the formula II

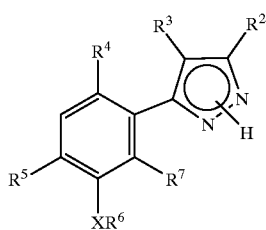

where R⁶ is hydroxyl, amino, —NE—Y—R⁸, hydroxylamino, —N(Y—R⁸)—OH, —NE—O—Z—R⁹, mercapto, —C(=NOH)—Y—R³, carboxyl, —CO—NE—O—Z—R⁹ or halosulfonyl.

If not stated otherwise, all the processes described above are advantageously carried out under atmospheric pressure or under the autogenous pressure of the reaction mixture in question.

The work-up of the reaction mixtures is usually carried out in a conventional manner. If not stated otherwise in the processes described above, the products of value are obtained, for example, after the dilution of the reaction solution with water by filtration, crystallization or solvent extraction, or by removing the solvent, partitioning the residue in a mixture of water and a suitable organic solvent and work-up of the organic phase to afford the product.

The 1-sulfonyl-3-phenylpyrazoles I can be obtained as isomer mixtures in the preparation; however, if desired, these can be separated into largely pure isomers using customary methods such as crystallization or chromatography, including chromatography over an optically active adsorbate. Pure optically active isomers can be prepared advantageously from suitable optically active starting materials.

Agriculturally useful salts of the compounds I can be formed by reaction with a base of the corresponding cation, preferably an alkali metal hydroxide or hydride, or by reaction with an acid of the corresponding anion, preferably of hydrochloric acid, hydrobromic acid, sulfuric acid, phosphoric acid or nitric acid.

Salts of I where the metal ion is not an alkali metal ion can be prepared by cation exchange of the corresponding alkali metal salt in a conventional manner, similarly ammonium, phosphonium, sulfonium and sulfoxonium salts by means of ammonia, phosphonium, sulfonium or sulfoxonium hydroxides.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds I, or herbicidal compositions comprising them, can additionally be employed in a further number of crop plants for eliuinating undesirable plants. Examples of suitable crops are the following: Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Dancus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Eumulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa , Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, SOrghum bicolor (s. vulgare), Theobroma cacao, Trifolium pratense, Triticum aestivum, Triticum durum, Vicia faba, vitis vinifera and Zea mays.

In addition, the compounds I may also be used in crops which tolerate the action of herbicides owing to breeding, including genetic engineering methods.

Moreover, the 1-sulfonyl-3-phenylpyrazoles I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is to facilitate harvesting, which is made possible by concentrating, over a period of time, dehiscence, or reducing the adherence to the tree, in citrus fruit, olives or other species and varieties of pomaceous fruit, stone fruit and nuts. The same mechanism, ie. promotion of the formation of abscission tissue between fruit or leaf and shoot of the plants, is also important for readily controllable defoliation of useful plants, in particular cotton.

Moreover, shortening the period within which the individual cotton plants mature results in improved fiber quality after harvesting.

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should guarantee the finest possible distribution of the active ingredients according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutyl-naphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributyl-phenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight of at least one active compound I. The active compounds are employed in a purity of from 90% to 100%, preferably 95% to 100% (according to NMR spectrum).

The formulation examples which follow illustrate the preparation of such products:

I. 20 parts by weight of the compound No. Ia.001 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. Ib.001 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. Id.002 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. Ie.001 are mixed thoroughly with 3 parts by weight of sodium diisobutylnaphthalene-a-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of the active ingredient No. Ie.002 are mixed with 97 parts by weight of finely divided kaolin. This gives a dust which comprises 3% by weight of active ingredient.

VI. 20 parts by weight of the active ingredient No. Ie.021 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. Ie.029 is dissolved in a mixture composed of 70 parts by weight of cyclohexanone, 20 parts by weight of ethoxylated isooctylphenol and 10 parts by weight of ethoxylated castor oil. The mixture can then be diluted with water to the desired concentration of active ingredient. This gives a stable emulsion concentrate.

VIII. 1 part by weight of the compound No. Ib.001 is dissolved in a mixture composed of 80 parts by weight of cyclohexanone and 20 parts by weight of Wettols EM 31 (=nonionic emulsifier based on ethoxylated castor oil). The mixture can then be diluted with water to the desired concentration of active ingredient. This gives a stable emulsion concentrate.

The active compounds I or the herbicidal compositions can be applied pre- or post-emergence. If the active ingredients are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active ingredients reach the leaves of undesirable plants growing underneath, or the bare soil surface (post-directed, lay-by).

The rates of application of active ingredient I are from 0.001 to 3.0, preferably 0.01 to 1.0, kg/ha of active substance (a.s.), depending on the control target, the season, the target plants and the growth stage.

To widen the spectrum of action and to achieve synergistic effects, the 1-sulfonyl-3-phenylpyrazoles I may be mixed with a large number of representatives of other herbicidal or growth-regulating active ingredients and then applied concomitantly. Suitable components for mixtures are, for example, 1,2,4-thiadiazoles, 1,3,4-thiadiazoles, amides, aminophosphoric acid and its derivatives, aminotriazoles, anilides, aryl-1 hetaryl- oxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta—$CF_3$-phenyl derivatives, carbamates, quinolinecarboxylic acid and its derivates, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Vonphytotoxic oils and oil concentrates may also be added.

PREPARATION EXAMPLES (The chemical shift [in ppm] of the nuclear magnetic resonance spectra was referenced to tetramethylsilane)

Example 1

3-(4-Chlorophenyl)-5-methyl-1-methylsulfonyl-1H-pyrazole (No. Ia.001)

0.27 g (11 mmol) of sodium hydride was added to a solution of 2 g (10 mmol) of 3(5)-(4-chlorophenyl)-5(3)-methyl-1H-pyrazole in 50 ml of tetrahydrofuran. After stirring for 10 minutes, the mixture was treated with 1.4 g (11 mmol) of methanesulfonyl chloride. The reaction mixture was then stirred for 16 hours and concentrated. The residue was taken up in 20 ml of water and 20 ml of ethyl acetate. The organic phase was separated off, washed with water and saturated brine, dried over magnesium sulfate and then concentrated. The crude product was purified by silica gel chromatography (eluent: hexanelethyl acetate=4:1). Yield 1.4 g; mp.: 96–97° C.

$^1$H NMR (400 MHz; in $CDC_{l3}$): δ [ppm]=2.59 (s,3H), 3.38 (s,3H), 6.44 (s,1H), 7.38 (d,2H), 7.76 (d,2H).

Intermediate: 3(5)-(4-Chlorophenyl)-5(3)-methyl-1H-pyrazole 79 g (0.6 mol) of potassium tert-butoxide were suspended in 200 ml of ethyl acetate. With considerable generation of heat, a solution was formed. At about 70° C., a solution of 50 g (0.32 mol) of 4-chloroacetophenone in 200 ml of ethyl acetate was then added dropwise and the mixture was stirred at 60° C. for 3 hours. Subsequently, the reaction mixture was poured into 1 l of 10% strength sulfuric acid. The product was then extracted twice with 200 ml of ethyl acetate each time. The combined organic phases were washed twice with water, dried over magnesium sulfate and finally concentrated. Yield of crude 1-(4-chlorophenyl)-butane-1,3-dione: 103 g.

72 g of this were dissolved in 300 ml of acetic acid and reacted with 18 g (0.36 mol) of hydrazine in an exothermic reaction. After the mixture had cooled to room temperature, it was poured into 2 l of ice-water. The precipitated crude product was filtered off and purified by recrystallization (twice) from hexane/ethyl acetate (2:1). Yield: 15 g; mp. 124–130° C.

$^1$H NMR (400 MHz; in $CDCl_3$): δ [ppm]=2.36 (s,3H), 5.50 (s,1H), 6.35 (s,1H), 7.36 (d,2H), 7.68 (d,23).

Example 2

4-Chloro-3-(4-chlorophenyl)-5-methyl-1-methylsulfonyl-1,1-pyrazole (No. Ib.001)

0.7 g (5.1 mmol) of sulfuryl chloride was added to a solution of 1.4 g (4.6 mmol) of 3-(4-chlorophenyl)-5-methyl-1-methylsulfonyl-1H-pyrazole in 50 ml of carbon tetrachloride. The reaction mixture was stirred for 2 hours and 100 ml of water were added. Subsequently, the organic phase was separated off, dried over magnesium sulfate and finally concentrated. Purification of the crude product was carried out by silica gel chromatography (eluent: hexane/ethyl acetate=6:1). Yield: 0.7 g; mp.: 100–102° C.

$^1$H NMR (400 MHz; in $CDCl_3$): δ [ppm]=2.58 (s,3H), 3.39 (s,3H), 7.43 (d,2H), 7.89 (d,2H).

Example 3

3-(4-Chloro-2-fluoro-5-methylphenyl)-5-methyl-1-methylsulfonyl-1H-pyrazole (No. Id.002)

Using 1.6 g (7.1 mmol) of 3(5)-(4-chloro-2-fluoro-5-methylphenyl)-5(3)-methyl-1B-pyrazole, 0.18 g (7.5 mmol) of sodium hydride and 0.81 g (7.1 mmol) of methanesulfonyl chloride and the method described in Example 1, 1 g of the abovementioned product of value was obtained.

$^1$H NMR (360 MHz, in $CDCl_3$): δ[ppm] =2.36 (s,3H), 2.58 (s,3H), 3.38 (s,3H), 6.56 (d,1H), 7.14 (d,1H), 7.90 (d,1H).

Intermediate 3.1: 4-(3-Chloro-2-fluoro-5-methylphenyl)butane-2,4-dione

A solution of 5 g (24 mmol) of 4-chloro-2-fluoro-5-methylbenzoyl chloride and 6.3 g (24 mmol) of copper(II) acetylacetonate in 150 ml of dichloromethane was stirred for 16 hours. Hydrogen sulfide was then passed into the reaction mixture until no more copper sulfide precipitated out (about 1 hour). The undissolved components were subsequently filtered off and the organic phase was dried over magnesium sulfate and concentrated. The residue was treated with 200 ml of a concentrated aqueous ammonia solution and then heated at reflux for 4 hours. The mixture was allowed to cool and extracted with dichloromethane. The organic phase was dried over magnesium sulfate and finally concentrated. The crude product was purified by silica gel chromatography (eluent:hexane/ethyl acetate=2:1). Yield: 2.2 g.

$^1$H NMR (250 MHz, in $CDCl_3$): δ[ppm]=2.07 (s,3H), 2.35 (s,3H), 5.68 (s,1H), 7.10 (d,1H), 7.67 (d,1H), 10.20 (s,1H).

Intermediate 3.2: 3(5)-(4-Chloro-2-fluoro-5-methylphenyl)-5(3)-methyl-1H-pyrazole A solution of 2.2 g (9.6 mmol) of 4-(3-chloro-2-fluoro-5-methylphenyl)butane-2,4-dione in 30 ml of glacial acetic acid was treated with 0.48 g (10 mmol) of hydrazine hydrate and then heated at reflux for 3 hours. The reaction mixture was subsequently poured into 1 l of water. The product of value was extracted from the resulting mixture with 100 ml of ethyl acetate. The extract was dried over magnesium sulfate and finally concentrated. Yield: 1.6 g.

$^1$H NMR (270 MHz, in CDCl$_3$): δ[ppm]=2.32 (s,3H), 2.34 (s,3H), 6.44 (d,1H), 7.14 (d,1H), 7.66 (d,1H).

Example 4

4-Chloro-3-(4-chloro-2-fluoro-5-methylphenyl)-5-methyl-1-methylsulfonyl-1H-pyrazole (No. Ie.002)

0.8 g (2.7 mmol) of 3-(4-chloro-2-fluoro-5-methylphenyl)-5-methyl-1-methylsulfonyl-1H-pyrazole and 0.4 g (3.0 mmol) of sulfuryl chloride were reacted in 50 ml of carbon tetrachloride by the method of Example 2. Yield: 0.1 g.

$^1$H NMR (270 MHz, in CDCl$_3$): δ[ppm]=2.37 (s,3H), 2.59 (s,3H), 3.39 (s,3H), 7.22 (d,1H), 7.42 (d, 1H).

Example 5

4-Chloro-3-(4-chloro-2-fluoro-5-propargyloxyphenyl)-5-methyl-1-methylsulfonyl-1H-pyrazole (No. Ie.021)

Using 0.4 g (1.3 mmol) of 4-chloro-3(5)-(4-chloro-2-fluoro-5-propargyloxyphenyl)-5(3)-methyl-1H-pyrazole, 35 mg (1.4 mmol) of sodium hydride and 0.14 g (1.3 imol) of methanesulfonyl chloride and the method described in Example 1, 0.3 g of the abovementioned product of value was obtained.

$^1$H NMR (400 MHz, in CDCl$_3$): δ[ppm]=2.57 (t,1H), 2.59 (s,3H), 3.41 (s,3H), 4.78 id,2H), 7.26 (m,2H).

Intermediate 5.1: 5-Bromo-2-chloro-4-fluorophenol 72.8 g (0.91 mol) of a 50% strength aqueous sodium hydroxide solution were added to a solution of 129 g (0.46 mol) of methyl (5-bromo-2-chloro-4-fluorophenyl) carbonate in 920 ml of methanol. The mixture was stirred for 30 minutes and then admixed with 0.4 l of water and subsequently concentrated to 600 ml. With ice-cooling, the mixture was acidified using 4% strength hydrochloric acid. The resulting product of value was then extracted with dichloromethane. The organic phase was dried over magnesium sulfate and finally concentrated. Yield: 78.7 g.

$^1$H NMR (250 MHz, in CDCl$_3$): δ[ppm]=5.38 (s,1E), 7.13 (d,1H), 7.25 (d,1H).

Intermediate 5.2: 1-Allyloxy-5-bromo-2-chloro-4-fluorobenzene 96.5 g (0.7 mol) of potassium carbonate and 54.9 g (0.45 mol) of allylbromide were added to a solution of 78.7 g (0.35 mol) of 5-bromo-2-chloro-4-fluorophenol in 350 ml of dimethylformamide. The reaction mixture was subsequently stirred for 1 hour and stirred into 2.5 l of water. The mixture was then extracted with dichloromethane (three times). The combined organic phases were washed with water (three times) and saturated aqueous sodium chloride solution (once), dried over magnesium sulfate and finally concentrated. The crude product was purified by distillation. Bp.: 106° C. (0.8 mbar); Yield: 85 g.

$^1$H NMR (270 MHz, in CDCl$_3$): δ[ppm]=4.57 (s,2H), 5.34 (d,1E), 5.46 (d,l1H), 6.04 (m,1H), 7.08 (d,1E), 7.19 (d,1E).

Intermediate 5.3: 5-Allyloxy-4-chloro-2-fluorobenzoic acid

At 20–25 C., 200 ml (0.4 mol) of a 2 M solution of isopropyl-magnesium chloride and tetrahydrofuran were added over a period of 30 minutes to a solution of 85 g (0.32 mol) of 1-allyloxy-5-bromo-2-chloro-4-fluorobenzene in 200 ml of tetrahydrofuran. The mixture was then stirred for 30 minutes and 50 g (1.1 mol) of dry ice were added with ice-cooling. The mixture was subsequently stirred for 16 hours, after which 250 ml of a 10% strength hydrochloric acid were added with ice-cooling. The aqueous phase was separated off and extracted with methyl tert-butyl ether. The combined organic phases were washed with saturated aqueous sodium chloride solution, dried over magnesium sulfate and finally concentrated. The crude product was purified by trituration with a little n-hexane and the precipitated product of value was filtered off. Yield: 59.7 g.

$^1$H NMR (250 MHz, in CDCl$_3$): δ[ppm]=4.66 (d,2H), 5.35 (d,1H), 5.49 (d,1H), 6.08 (m,1H), 7.26 (d,1E), 7.52 (d,1E).

Intermediate 5.4: 5-Allyloxy-4-chloro-2-fluorobenzoyl chloride

With ice-cooling, 1 drop of dimethylformamide and 49.2 g (0.38 mol) of oxalyl chloride were added in succession to a solution of 59.7 g (0.26 mol) of 5-allyloxy-4-chloro-2-fluorobenzoic acid in 0.5 l of toluene. After the evolution of gas had ceased, the mixture was concentrated to about half its volume. In this form, the product solution was used for the next step.

Intermediate 5.5: 4-(5-Allyloxy-4-chloro-2-fluorophenyl) butane-2,4-dione

Using the acyl chloride solution prepared as intermediate 5.4 and 68 g (0.26 mol) of copper(II) acetylacetonate and the method described for intermediate 3.1, a triketone was obtained which was subsequently reacted with 0.3 l of concentrated aqueous ammonia solution. Yield: 22.5 g.

$^1$H NMR (270 MHz, in CDCl$_3$): δ[ppm]=2.07 (s,3E), 2.65 (d,1H), 5.32 (d,1H), 5.47 (d,1H), 5.72 (d,1H$_1$), 6.06 (m,1B), 7.14 (d,1E), 7.42 (d,1H), 10.22 (s,1B).

Intermediate 5.6: 3(5)-(5-Allyloxy-4-chloro-2-fluorophenyl)-5(3)-methyl-1H-pyrazole 22.5 g (83 mmol) of 4-(5-allyloxy-4-chloro-2-fluorophenyl)butane-2,4-dione and 4.3 g (85 mmol) of hydrazine hydrate were reacted by the method described for intermediate 3.2. Yield: 20.2 g. 1H NMR (270 MHz, in CDCl$_3$): δ[ppm]=2.32 (d,3E), 4.53 (d,1H), 5.28 (d,1H), 5.41 (d,1l), 6.03 (m,1H), 6.47 (d,1H), 7.18 (d$_{1,\,1}$H), 7.38 (d,1H).

Intermediate 5.7: 3(5)-[4-Chloro-2-fluoro-5-(1-propen-1-yloxy)-phenyl]-5(3)-methyl-1H-pyrazole 11.2 g (0.1 mol) of potassium tert-butoxide were added to a solution of 13 g (49 mmol) of 3(5)-(5-allyloxy-4-chloro-2-fluorophenyl)-5(3)-methyl-1H-pyrazole in 50 ml of dimethyl sulfoxide. The reaction mixture was stirred for 16 hours and then treated with saturated aqueous ammonium chloride solution. The resulting solid product of value was subsequently separated off.

Yield: quantitative.

$^1$H NMR (200 MHz, in CDCl$_3$): δ[ppm]=1.73 (dd,3H), 2.34 (d,3H), 4.80 (s,1H), 4.95 (dq,1H), 6.30 (dq,1H), 6.46 (dd,1H), 7.21 (d,1H), 7.49 (d,1H).

Intermediate 5.8: 2-Chloro-4-fluoro-5-[5(3)-methyl-1H-pyrazol-3(5)-yl]phenol 27 ml of concentrated hydrochloric acid were added to a solution of 13 g (49 mmol) of 3(5)-[4-chloro-2-fluoro-5-(1-propen-1-yloxy)phenyl]-5(3)-methyl-1H-pyrazole in 150 ml of ethanol. The reaction mixture was stirred at room temperature for 1.5 hours and then concentrated. The residue was admixed with 50 ml of water and subsequently extracted with ethyl acetate (four times). The combined organic phases were dried over magnesium sulfate and finally concentrated. Yield: 10.4 g.

$^1$H NMR (250 MHz, in d$^6$-dimethyl sulfoxide): δ[ppm] =2.27 (s,3H), 5.50 (s,2H), 6.35 (d,1H), 7.34 (d,1H), 7.52 (d,1H).

Intermediate 5.9: 2-Chloro-4-fluoro-5-(4-chloro-5(3)-methyl-1H-pyrazol-3(5)-yl)phenol 1.2 g (8.7 mmol) of sulfuryl chloride were added to a suspension of 1.8 g (7.9 mmol) of 2-chloro-4-fluoro-5-(5(3)-methyl-1H-pyrazol-3(5)-yl)phenol in 100 ml of 1,2-dichloroethane and the mixture was heated at reflux temperature for 5 hours. The reaction mixture was subsequently concentrated and the crude product was purified by silica gel chromatography (eluent:ethyl acetate/hexane=4:1). Yield: 0.6 g.

$^1$H-NMR (270 MHz, in CDCl$_3$): δ[ppm]=2.33 is,3H), 7.21 (d,1H), 7.50 (d,1H).

Intermediate 5.10: 4-Chloro-3(5)-(4-chloro-2-fluoro-5-propargyloxyphenyl)-5(3)-methyl-1H-pyrazole 0.63 g (46 mmol) of potassium carbonate, 0.27 g (2.3 mmol) of propargyl bromide and a spatula tip of sodium iodide were added to a solution of 0.6 g (2.3 mmol) of 2-chloro-4-fluoro-5-(4-chloro-5(3)-methyl-1H-pyrazol-3(5)-yl)phenol in 50 ml of dimethylformamide. The reaction mixture was subsequently stirred at 80° C. for 3 hours and then poured into 100 ml of water. The mixture was extracted with ethyl acetate (three times). The combined extracts were washed with water (three times), dried over magnesium sulfate and finally concentrated. The crude product was purified by silica gel chromatography (eluent:hexane/ethyl acetate=4:1). Yield: 0.4 g.

$^1$H NMR (250 MHz, in CDCl$_3$): δ[ppm]=2.34 (s,3E), 2.55 (t,1E), 4.80 (d,2H), 7.28 (d,1H), 7.65 (d,1E).

Example 6

Methyl 2-chloro-4-fluoro-5-(4-chloro-5-methyl-1-ethylsulfonyl-1H-pyrazol-3-yl)phenoxyacetate (No. Ie.029)

Using 0.2 g (0.62 mmol) of methyl 2-chloro-4-fluoro-5-(4-chloro-5(3)-methyl-1H-pyrazol-3(5)-yl)phenoxyacetate, 16 mg (0.65 nmol) of sodium hydride and 71 mg (0.62 mmol) of methanesulfonyl chloride and the method of Example 1, 0.2 g of the desired product of value was obtained.

1H NMR (250 MHz, in CDCl$_3$): δ[ppm] 2.59 (s,3H), 3.40 (s,3H), 3.81 (s,3H), 4.74 (s,2B), 7.06 (d,1H), 7.28 (d,1H).

Intermediate: Methyl 2-chloro-4-fluoro-5-(4-chloro-5(3)-methyl-1H-pyrazol-3(5)-yl)phenoxyacetate Using 2.3 g (8.8 mmol) of 2-chloro-4-fluoro-5-(4-chloro-5(3)-methyl-1H-pyrazol-3(5)-yl)phenol, 2.4 g (17.6 mmol) of potassium carbonate, 1.35 g (8.8 mmol) of methyl bromoacetate and a spatula tip of sodium iodide and the method for preparing intermediate 5.10, 0.2 g of the desired product of value was obtained.

$^1$H NMR (400 MHz, in d6-dimethyl sulfoxide): δ[ppm]= 2.28 (s,3H), 3.72 (s,3H), 5.00 (s,2H), 7.16 (m,iB), 7.59 (m,1H), 13.2S (s,1E).

Example 7

4-Chloro-3-(4-chloro-2-fluorophenyl)-5-methyl-1-methylsulfonyl-1H-pyrazole (No. Ie.001)

Using 0.8 g (3.3 mmol) of 4-chloro-3(5)-(4-chloro-2-fluorophenyl)-5(3)-methyl-1H-pyrazole, 83 mg (3.4 mmol) of sodium hydride and 0.37 g (3.3 mmol) of methanesulfonyl chloride and the method described in Example 1, 0.4 9 of the desired product of value was obtained.

$^1$H NMR (250 MHz, in CDCl$_3$): δ[ppm]=2.59 (s,3H), 3.40 (s,3H), 10 7.20 (m,2H), 7.51 (t,1H).

Intermediate: 4-Chloro-3(5)-(4-chloro-2-fluorophenyl)-5(3)-methyl-1H-pyrazole

A solution of 1.8 g (8.6 mmol) of 3(5)-(4-chloro-2-fluorophenyl)-5(3)-methyl-1H-pyrazole and 1.3 g (9.5 mmol) of sulfuryl chloride in 40 ml of carbon tetrachloride was stirred for 30 minutes in an ultrasonic bath and then concentrated. Yield: 2 g of the desired intermediate.

$^1$H NMR (250 MHz; in CDCl$_3$): δ[ppm] 2.42 (s,3H), 7.20 (m,2H, 7.66 (t,1H).

Use examples (herbicidal activity)

The herbicidal activity of the 1-sulfonyl-3-phenylpyrazoles I was demonstrated by the following greenhouse experiments:

The culture containers used were plastic flowerpots containing loamy soil with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with translucent plastic hoods until the plants had rooted. This cover causes uniform germination of the test plants, unless this was adversely affected by the active ingredients.

For the post-emergence treatment, the test plants were first grown to a plant height of 3 to 15 cm, depending on the plant habit, and only then treated with the active ingredients which had been suspended or emulsified in water. The test plants for this purpose were either sown directly and grown in the same containers, or they were first grown separately as seedlings and transplanted into the test containers a few days prior to the treatment. The rate of application for the post-emergence treatment was 0.5 kg/ha of a.s. (active substance).

Depending on the species, the plants were kept at from 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific name | Common name |
| --- | --- |
| *Echinochloa crus-galli* | barnyard grass |
| *Galium aparine* | catchweed bedstraw |
| *Ipomoea subspecies* | morning glory |
| *Setaria italica* | foxtail millet |

The compound No. Ib.001, applied post-emergence, showed a very 25 good herbicidal activity against the abovementioned undesirable plants at a rate of application of 0.5 kg/ha of a.s.

Use Examples (desiccant/defoliant activity)

The test plants used were young cotton plants with 4 leaves (without cotyledons) which had been grown under greenhouse conditions (relative atmospheric humidity 50 to 70%; day/night temperature 27/20° C.).

The young cotton plants were subjected to foliar treatment to runoff point with aqueous preparations of the active ingredients (with an addition of 0.15% by weight of the fatty alcohol alkoxide Pluraface LF 700 1), based on the spray mixture). The amount of water applied was 1000 l/ha (converted). After 13 days, the number of leaves shed and the degree of defoliation in % were determined.

No leaves were shed in the untreated control plants.

We claim:

1. 1-Sulfonyl-3-phenylpyrazoles of the formula I

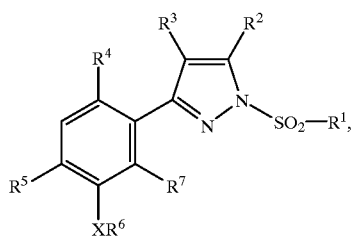

where:
$R^1$ is $C_1$–$C_4$-alkyl or $C_1$–$C_4$-haloalkyl;
$R^2$ is $C_1$–$C_4$-alkyl or $C_1$–$C_4$-haloalkyl;
$R^3$ is hydrogen, cyano, halogen or $C_1$–$C_4$-alkyl;
$R^4$ is hydrogen or halogen;
$R^5$ is hydrogen, cyano, nitro, halogen, $C_1$–$C_4$-alkyl, $C_1$–$C_4$-haloalkyl, $C_1$–$C_4$-alkoxy or $C_1$–$C_4$-haloalkoxy;
X is a chemical bond or a methylene, ethylene, propane-1,3-diyl or ethene-1,2-diyl chain or an oxymethylene or thiamethylene chain linked to the phenyl ring via the hetero atom, all chains being unsubstituted or substituted by one or two substituents selected in each case from the group consisting of cyano, carboxyl, halogen, $C_1$–$C_4$-alkyl, $C_1$–$C_4$-haloalkyl, $C_1$–$C_4$-alkoxy, ($C_1$–$C_4$-alkoxy)carbonyl, di($C_1$–$C_4$-alkyl)amino and phenyl;
$R^6$ is hydrogen, nitro, cyano, halogen, halosulfonyl, —O—Y—$R^8$, —O—CO—Y—$R^8$, —N(Y—$R^8$)(Z—$R^9$), —N(Y—$R^8$)—SO$_2$—Z—$R^9$, —N(SO$_2$—Y—$R^4$) (SO$_2$—Z—$R^9$), —N(Y—$R^8$)—CO—Z—$R^9$, —N(Y—$R^8$)(O—Z—$R^9$), —S—Y—$R^8$, —SO—Z—$R^8$, —SO$_2$—Y—$R^8$, —SO$_2$—O—Y—$R^8$, —SO$_2$—N(Y—$R^8$)(Z—$R^9$), —CO—Y—$R^8$, —C(=NOR10)—Y—$R^8$, —C(=NOR$^1$)—O—Y—$R^8$, —C—O—Y—$R^8$, —CO—S—Y—$R^8$, —CO—N(Y—$R^8$)(Z—$R^9$), —CO—N(Y—$R^8$)(O—Z—$R^9$) or PO(O—Y—$R^8$)$_2$;
$R^7$ is hydrogen,
or $R^5$ and $XR^6$ or $XR^6$ and $R^7$ form together with the carbons of the phenyl ring linking them a fused carbocyclic or 5- or 6-membered heterocyclic ring having 1 to 3 hetero atoms selected from a group consisting of one to three nitrogens, one or two oxygens and one or two sulfur atoms, the fused ring being unsubstituted or substituted by one or two substituents selected in each case from the group consisting of Ci–$C_4$-alkyl, $C_1$–$C_4$-haloalkyl, $C_2$–$C_6$-alkenyl, $C_2$–$C_6$-haloalkenyl, $C_2$–$C_6$-alkynyl, $C_1$–$C_4$-alkoxy, Ci–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl, $C_1$–$C_4$-haloalkylsulfonyl, ($C_1$–$C_4$-alkoxy) carbonyl, ($C_1$–$C_4$-alkoxy)carbonyl—$C_1$–$C_4$-alkyl, phenyl and phenyl—$C_1$–$C_4$-alkyl, it being possible for the fused cycle to contain one or two non-neighboring carbonyl, thiocarbonyl or sulfonyl ring members;

Y and Z are each independently of each other a chemical bond or a methylene or ethylene chain which may be unsubstituted or substituted by one or two substituents selected in each case from the group consisting of carboxyl, $C_1$–$C_4$-alkyl, $C_1$–$C_4$-haloalkyl, ($C_1$–$C_4$-alkoxy)carbonyl and phenyl;

$R^8$ and $R^9$ are each independently of each other hydrogen, $C_1$–$C_6$-haloalkyl, $C_2$–$C_6$-alkenyl, $C_2$–$C_1$-haloalkenyl, $C_2$–$C_6$-alkynyl, $C_2$–$C_6$-haloalkynyl, —CH($R^{11}$)($R^{12}$), —C($R^{11}$)($R^{12}$)—NO$_2$, —C($R^{11}$)($R^{12}$)—CN, —C($R^{13}$) ($R^{12}$)-halogen, —C($R^{11}$)($R^{12}$)—OR$^{13}$, —C($R^{11}$) ($R^{12}$)—N ($R^{13}$) $R^{14}$, —C ($R^{11}$)($R^{12}$)—N ($R^{13}$) —OR$^{14}$, —C($R^{11}$)($R^{12}$)—SR$^{13}$, —C ($R^{11}$)($R^{12}$) —SO—R$^{13}$, —C ($R^{11}$)($R^{12}$) —SO$_2$—R$^{13}$, —C($R^{11}$)($R^{12}$)—SO$_2$—OR$^{13}$, —C ($R^{11}$)($R^{12}$)—SO$_2$—N ($R^{13}$) $R^{14}$, —C($R^{11}$) ($R^{12}$)—CO—R$_{13}$, —C($R^{11}$)($R^{12}$)—C (=NOR$^{15}$)—R$_{13}$, —C($R^{11}$)($R^{12}$)—CO—OR$^{13}$, —C ($R^{1/}$)($R^{12}$)—CO—SR$^{13}$, —C($R^{11}$)($R^{12}$)—CO—N ($R^{13}$)$R^{14}$, —C($R^{11}$)($R^{12}$) —CO—N ($R^{13}$) —OR$^{14}$, —C($R^{11}$) ($R^{12}$)—PO OR$^{13}$)$_2$, $C_3$–$C_8$-cycloalkyl which may contain a carbonyl or thiocarbonyl ring member, phenyl or 3- to 7-membered heterocyclyl which may contain a carbonyl or thiocarbonyl ring member, the cycloalkyl, phenyl and heterocyclyl rings being in each case unsubstituted or substituted by one to four substituents selected in each case from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl) carbonyloxy, ($C_1$–$C_4$-alkoxy) carbonyl and di-($C_1$–$C_4$-alkyl) amino;

$R^{10}$ is hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalkyl, phenyl or phenyl $C_1$–$C_4$-alkyl; $R^{11}$ and $R^{12}$ are each independently of each other hydrogen, $C_1$–$C_4$-alkyl, $C_1$–$C_4$-alkoxy—$C_1$–$C_4$-alkyl, $C_1$–$C_4$-alkylthio—$C_1$–$C_4$-alkyl, ($C_1$–$C_4$-alkoxy)carbonyl-$C_1$–$C_4$-alkyl or phenyl—$C_1$–$C_4$-alkyl, the phenyl ring being unsubstituted or substituted by one to three substituents selected in each case from the groud consisting of cyano, nitro, carboxyl, halogen, $C_1$–$C_4$-alkyl, $C_1$–$C_4$-haloalkyl and ($C_1$–$C_4$-alkoxy) carbonyl;

$R^{13}$ and $R^{14}$ are each independently of each other hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_6$-haloalkynyl, $C_3$–$C_8$-cycloalkyl, $C_3$–$C_8$-cycloalkyl—$C_1$–$C_4$-alkyl, phenyl, phenyl—$C_1$–$C_4$-alkyl, 3- to 7-membered heterocyclyl or heterocyclyl–$C_1$–$C_4$-alkyl, where each cycloalkyl and each heterocyclyl ring may contain a carbonyl or thiocarbonyl ring member and where the cycloalkyl, phenyl and heterocyclyl rings may in each case be unsubstituted or substituted by one to four substituents selected in each case from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-haloalkyl)carbonyl, ($C_1$–$C_4$-alkyl) carbonyloxy, ($C_1$–$C_4$-haloalkyl) carbonyloxy, ($C_1$–$C_4$-alkoxy) carbonyl and di ($C_1$–$C_4$-alkyl) amino;

$R^{15}$ is hydrogen, $C_1$–$C_6$-alkyl, $C_1$–$C_6$-haloalkyl, $C_2$–$C_6$-alkenyl, $C_2$–$C_6$-haloalkenyl, $C_2$–$C_6$-alkynyl, $C_2$–$C_4$-haloalkynyl, $C_3$–$C_8$-cycloalkyl, phenyl or phenyl—$C_1$–$C_4$-alkyl;

and agriculturally useful salts of I.

2. A herbicidal composition comprising a herbicidally active amount of at least one 1-sulfonyl-3-phenylpyrazole of the formula I or of an agriculturally useful salt of I, as claimed in claim 1, and at least one inert liquid and/or solid carrier and, if desired, at least one surfactant.

3. A composition for the desiccation and/or defoliation of plants, comprising such an amount of at least one 1-sulfonyl-3-phenylpyrazole of the formula I or an agriculturally useful salt of I, as claimed in claim 1, that it acts as a desiccant and/or defoliant, and at least one inert liquid and/or solid carrier and, if desired, at least one surfactant.

4. A process for preparing herbicidally active compositions, which comprises mixing a herbicidally active amount of at least one 1-sulfonyl-3-phenylpyrazole of the formula I or an agriculturally useful salt of I, as claimed in claim 1, and at least one inert liquid and/or solid carrier and, if desired, at least one surfactant.

5. A process for preparing compositions which act as desiccants and/or defoliants, which comprises mixing such an amount of at least one 1-sulfonyl-3-phenylpyrazole of the formula I or an agriculturally useful salt of I, as claimed in claim 1, that it acts as a dessicant and/or defoliant, with at least one inert liquid and/or solid carrier and, if desired, at least one surfactant.

6. A method for controlling undesirable vegetation, which comprises allowing a herbicidally active amount of at least one 1-sulfonyl-3-phenylpyrazole of the formula I or of an agriculturally useful salt of I, as claimed in claim 1, to act on plants, their habitat or on seeds.

7. A method for the desiccation and/or defoliation of plants, which comprises allowing such an amount of at least one 1-sulfonyl-3-phenylpyrazole of the formula I or of an agriculturally useful salt of I, as claimed in claim 1, to act on plants that it has a desiccant and/or defoliant action.

8. A method as claimed in claim 7, wherein cotton is treated.

9. A process for preparing 1-sulfonyl-3-phenylpyrazoles of the formula I, as claimed in claim 1, where $R^3$ is halogen, which comprises halogenating the corresponding 1-sulfonyl-3-phenyl-pyrazoles I where $R^3$=hydrogen.

10. A process for preparing 1-sulfonyl-3-phenylpyrazoles of the formula I, as claimed in claim 1, which comprises reacting a phenylpyrazole of the formula II

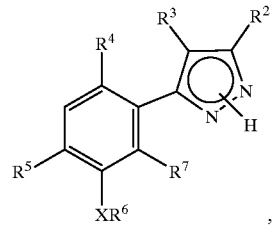

where $R^2$—$R^2$ and X are as defined in claim 1 and the circle in the pyrazole ring represents two double bonds, in the presence of a base with a sulfonic acid derivative L—$SO_2$—$R^1$ (formula III) where $R^1$ is as defined in claim 1 and L is a customary leaving group.

* * * * *

UNITED STATES PATENT AND TRADEMARK OFFICE
CERTIFICATE OF CORRECTION

PATENT NO. : 6,054,413
DATED : April 25, 2000
INVENTOR(S) : ZAGAR et al.

It is certified that error appears in the above-indentified patent and that said Letters Patent is hereby corrected as shown below:

Column 49, claim 1, line 42, change "$R^4$" to --$R^8$--.

Column 49, claim 1, line 46, change "(=NOR10)" to --(=$NOR^{10}$)--.

Column 49, claim 1, line 47, change "(=$NOR^1$)-O-Y-$R^8$, -C-O-Y-$R^8$" to --(=$NOR^{10}$)-O-Y-$R^8$, -CO-O-Y-$R^8$--.

Column 49, claim 1, line 58, change "$C_i$" to --$C_1$--.

Column 49, claim 1, line 61, change "alkylsulf inyl" to --alkylsulfinyl--.

Column 50, claim 1, line 8, change "$C_2$-$C_1$" to --$C_2$-$C_6$--.

Column 50, claim 1, line 10, change "-C($R^{13}$)" to -- -C($R^{11}$)--.

Column 50, claim 1, line 42, change "groud" to --grasp--.

Column 50, claim 1, line 65, change "$C_4$" to --$C_6$--.

Signed and Sealed this

Third Day of April, 2001

Attest:

NICHOLAS P. GODICI

*Attesting Officer*  *Acting Director of the United States Patent and Trademark Office*